(12) United States Patent
Hong et al.

(10) Patent No.: US 7,279,588 B2
(45) Date of Patent: Oct. 9, 2007

(54) DINUCLEAR METAL COMPLEX AND PYROPHOSPHATE ASSAY USING THE SAME

(75) Inventors: Jong-In Hong, Seoul (KR); Dong Hoon Lee, Seoul (KR); Ja Hyun Im, Seoul (KR); Seung Uk Son, Seoul (KR); Young Keun Chung, Seoul (KR)

(73) Assignee: Seoul National University Foundation, Seoul (KR)

( * ) Notice: Subject to any disclaimer, the term of this patent is extended or adjusted under 35 U.S.C. 154(b) by 590 days.

(21) Appl. No.: 10/855,940

(22) Filed: May 27, 2004

(65) Prior Publication Data

US 2005/0119497 A1 Jun. 2, 2005

(30) Foreign Application Priority Data

Dec. 2, 2003 (KR) ...................... 10-2003-0086782
May 17, 2004 (KR) ...................... 10-2004-0034773

(51) Int. Cl.
*C07F 1/00* (2006.01)
*C07F 15/00* (2006.01)
*D06L 1/00* (2006.01)

(52) U.S. Cl. ..................... 556/17; 556/21; 556/135; 556/136; 556/148; 556/150; 556/34; 424/9.1; 424/9.6

(58) Field of Classification Search ................. 556/17, 556/21, 135, 136, 148, 150, 34; 424/9.1, 424/9.6
See application file for complete search history.

(56) References Cited

OTHER PUBLICATIONS

Lee et al., Angew. Chem. Int. Ed., vol. 43, No. 36, pp. 4777-4780 (Sep. 13, 2004).*
Johansson et al, Synthesis and Photophysics of One Mononuclear Mn(III) and One Dinuclear Mn(III,III) Complex Covalently Linked to a Ruthenium (II) Tris(bipyridyl) Complex, Inorganic Chemistry, vol. xx, No. xx,xxxx, pp. A-J, 1998.

(Continued)

*Primary Examiner*—Porfirio Nazario-Gonzalez
(74) *Attorney, Agent, or Firm*—Ladas & Parry LLP

(57) ABSTRACT

A novel coordination complex formed by dinuclear metal complexation is provided. The complex is a dinuclear metal complex of a compound, wherein the compound comprises a conjugation ring system substituted with: a) an electron donating group selected from —OH, —SH and —NH$_2$; b) an indicating group selected from a chromogenic group, a fluorescent group and an electrochemical group; and c) two binding auxiliary groups, in combination with the electron donating group each of which being coordinated with the metal to provide an anion bonding site, wherein as the complex binds to a anion, the coordination of the electron donating group with the metal is weakened and electron donation of the electron donating group to the conjugation ring system is reinforced such that the reinforced electron donation by the electron donating group is transferred through the conjugation ring system to the indicating group to produce an indicating signal concomitant with the change of its electronic density. The coordination complex shows high sensitivity and high selectivity for pyrophosphate over other anions in an aqueous solvent over a wide pH range. Therefore, the complex is useful for pyrophosphate assay as a pyrophosphate sensor.

20 Claims, 12 Drawing Sheets
(1 of 12 Drawing Sheet(s) Filed in Color)

(a)

(b)

OTHER PUBLICATIONS

Lambert et al, Synthesis, Structural, Magnetic, And Redox Properties Of Asymmetric Diiron Complexes With A Single Terminally Bound Phenolate Ligand. Relevance To The Purple Acid Phosphatase Enzymes, J. Am. Chem. Soc., vol. 119, No. 40, pp. 9424-9437, 1997.

Seo et al, "Structure and Reactivity of a Dinuclear Cobalt(III) Complex with a Bridging Phosphate Monoester", Inorganic Chemistry, vol. 35, No. 26, pp. 7472-7473, 1996.

Mashuta et al, "Electron Transfer in $Fe^{II}Fe^{III}$ Model Complexes of Iron-Oxo Proteins", J. Am. Chem. Soc., vol. 114, No. 10, pp. 3815-3827, 1992.

Iranzo et al, "Physical And Kinetic Analysis Of The Cooperative Role Of Metal Ions In Catalysis Of Phosphodiester Cleavage By A Dinuclear Zn(II) Complex", J. Am. Chem. Soc., vol. 125, No. 7, pp. 1988-1993, 2003.

* cited by examiner a)

b)

US 7,279,588 B2

DINUCLEAR METAL COMPLEX AND PYROPHOSPHATE ASSAY USING THE SAME

TECHNICAL FIELD OF THE INVENTION

The present invention relates to a dinuclear metal complex, more particularly, to a dinuclear metal complex useful for pyrophosphate assay. The present invention also relates to a pyrophosphate assay using the dinuclear metal complex.

BACKGROUND OF THE INVENTION

The development of receptors for biologically important anions is emerging as a research area of great importance.[1] Pyrophosphate anion (hereinafter "PPi"), in particular, participates in several bioenergetic and metabolic processes,[2] such as the synthesis of cyclic AMP as a second messenger from ATP with the concomitant release of PPi and the production of calcium pyro-phosphate dihydrate (CPPD) crystals.[3] It is the deposition of CPPD crystals that is frequently detected in patients with osteoarthropathy or pseudogout.[3] This diversity of function, both beneficial and otherwise, is why the detection of PPi is the main focus of many research groups today. While PPi analysis such as ion chromatography remains important, there is mounting incentive to find alternative means of analysis, including those based on the use of selective chemosensors.[1b,4] Particularly useful would be systems that can recognize PPi in an aqueous solution and signal its presence via various signals (for example, an optical signal, a fluorescent signal and an electrical signal). Until now, very few examples of sensors for PPi in aqueous solution have been reported.[5,6] Further, the sensors failed to give satisfactory results.

Suitable PPi sensor should satisfy the following requirements:

(1) High selectivity for the pyrophosphate anion over other anions;
(2) High sensitivity for the pyrophosphate anion over other anions;
(3) Sufficient compatibility to an aqueous system; and
(4) Applicability over a wide pH range or insensitivity to pH change.

SUMMARY OF THE INVENTION

An object of the present invention is to provide a pyrophosphate sensor which satisfies the above requirements. The pyrophosphate sensor according to the present invention is a coordination complex formed by dinuclear metal complexation. More particularly, the complex is a dinuclear metal complex of a compound, wherein the compound comprises a conjugation ring system substituted with: a) an electron donating group selected from —OH, —SH and —NH$_2$; b) an indicating group selected from a chromogenic group, a fluorescent group and an electrochemical group; and c) two binding auxiliary groups, in combination with the electron donating group each of which being coordinated with the metal to provide an anion bonding site. As the complex binds to the anion, the coordination of the electron donating group with the metal is weakened and electron donation of the electron donating group to the conjugation ring system is reinforced. The reinforced electron donation by the electron donating group is transferred through the conjugation ring system to the indicating group to produce a detectable indicating signal concomitant with the change of its electronic density. Such a fact was demonstrated by X-ray analysis. As the PPi anion binds to the anion binding site of the dinuclear metal complex, the coordination between the electron donating group and the metal is weakened. This induces negative charge character to the electron donating group and electron donation by the electron donating group is reinforced. The reinforced electron donation by the electron donating group is transferred through the conjugation ring system to the indicating group, which results in the increase of its electronic density (or configuration). Due to the increased electronic density (or change of electronic configuration), the indicating group produces a detectable indicating signal such as a color change, a fluorescent signal or an electrical signal. According to a preferred embodiment of the present invention, the conjugation ring system is an aromatic ring system. More preferably, the conjugation ring system is a benzene ring system in which each of the two binding auxiliary groups is substituted at an ortho position and the indicating group is at a para position relative to the electron donating group.

According to a further preferred embodiment, there is provided a dinuclear metal complex of a compound having formula I:

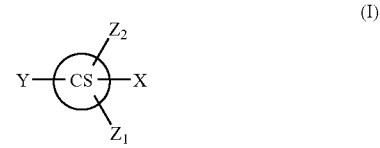

wherein, X is an electron donating group selected from —OH, —SH and —NH$_2$; Y is an indicating group selected from a chromogenic group, a fluorescent group and an electrochemical group; $Z_1$ and $Z_2$ are binding auxiliary groups, both of which are each independently hydrocarbons containing at least one atom selected from the group consisting of N, O, S and P; and

is a conjugation ring system.

According to another preferred embodiment of the present invention, there is provided a dinuclear metal complex of a compound having formula II:

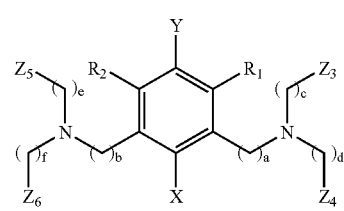

wherein, X is an electron donating group selected from —OH, —SH and —NH$_2$; Y is an indicating group selected from a chromogenic group, a fluorescent group and an electrochemical group; $Z_3$, $Z_4$, $Z_5$ and $Z_6$ are each independently hydrocarbons containing at least one atom selected from the group consisting of N, O, S and P; $R_1$ and $R_2$ are each independently selected from the group consisting of hydrogen, halogen, hydroxyl, amino, alkyl, alkoxy, thioalkyl, alkylamino, imine, amide, phosphate, phosphine, carbonyl, carboxyl, silyl, ether, thioether, sulfonyl, selenoether and ketone; and a, b, c, d, e and f are each independently integers of 1 to 3, more preferably 1 or 2.

The present invention also provides a method for assaying pyrophosphate anion. The method comprises adding a pyrophosphate sensor to a sample to be tested to generate a detectable indicating signal followed by detecting the indicating signal to quantify the pyrophosphate anion, characterized in that the pyrophosphate sensor is the above-mentioned dinuclear metal complex.

BRIEF DESCRIPTION OF THE DRAWINGS

The patent or application file contains at least one drawing (or color photograph) executed in color. Copies of this patent or patent application publication with color drawings(s) will be provided by the Office upon request and payment of the necessary fee.

DETAILED DESCRIPTION OF THE INVENTION

I. Definitions

Figure 1:
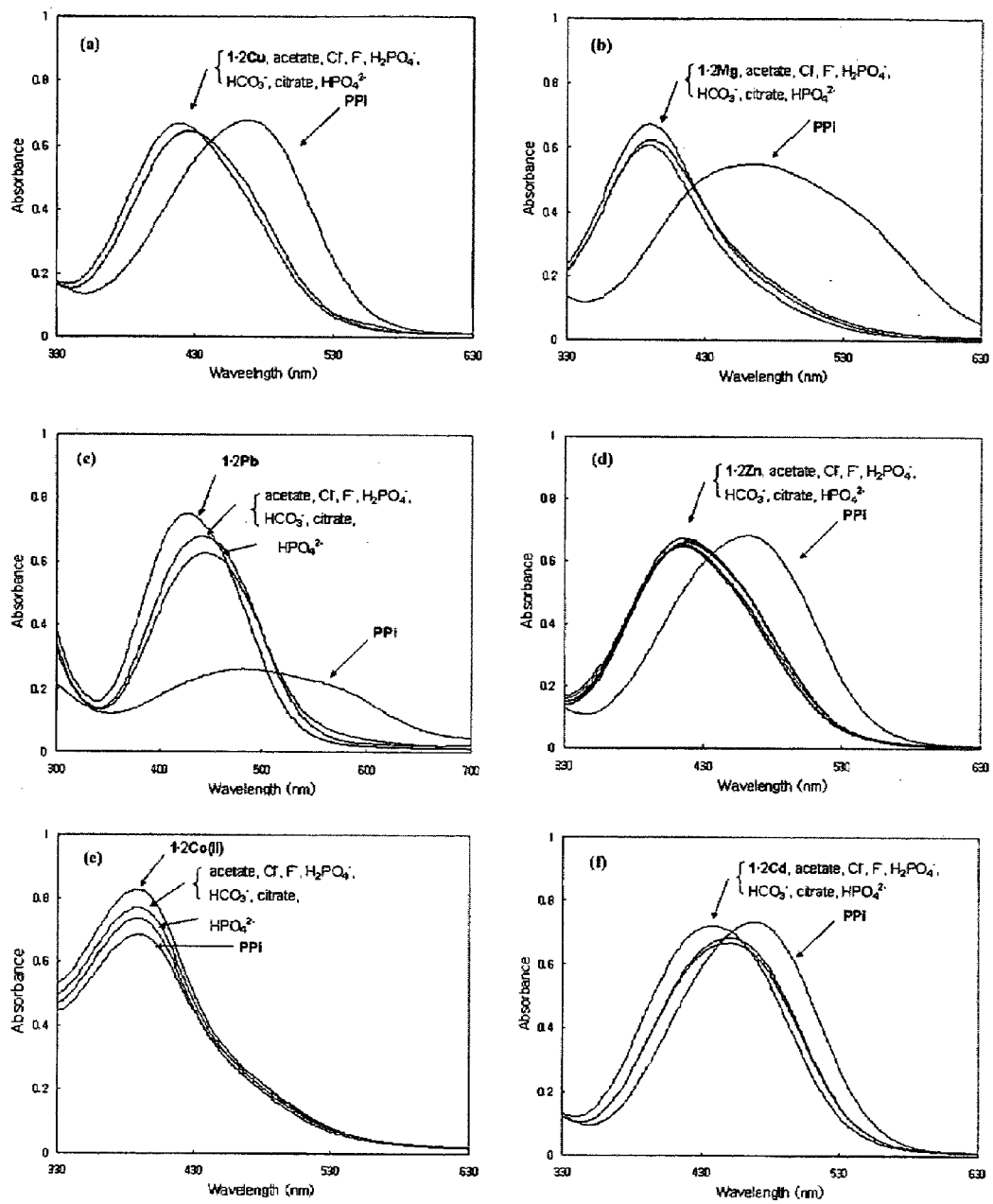
FIG. 1 is UV-vis spectra showing absorption changes of: (a) 1•2Cu; (b) 1•2Mg; (c) 1•2Pb; (d) 1•2Zn (e) 1•2Co(II); and (f) 1•2Cd in the presence of various anions. The spectra were measured in pure aqueous solution of 10 mM HEPES buffer (pH 7.4) at 25° C., respectively.

The following includes definitions of exemplary terms used throughout the disclosure. Both singular and plural forms of all terms fall within each meaning:

"Conjugation ring system," as used herein, means a system that when local electron richness or deficiency is occurred at a certain position within the ring system, conjugation occurs within the ring system to counteract the local electron richness or deficiency. For example, when local electron richness occurs at a certain position within the ring system, conjugative distribution of the electron to another position of the ring system takes place in order to stabilize the ring system.

"Aromatic ring system," as used herein, means a ring system having an aromaticity. The system satisfies so called "Hückel 4n+2 rule." The system includes a hydrocarbon aromatic ring system and hetero-aromatic ring system bearing at least one and up to four non-carbon atoms selected from oxygen, sulfur and nitrogen. Examples of the hydrocarbon aromatic ring system include benzene, indene, naphthalene, anthracene, phenanthrene, and the likes. Examples of hetero-aromactic ring system include thiene, furan, pyrrole, imidazole, pyrazole, thiazole, isothiazole, oxazole, isoxazole, triazole, thiadiazole, oxadiazole, tetrazole, thiatriazole, oxatriazole, pyridine, pyrimidine, pyrazine, pyridazine, triazine, tetrazine, quinoline, isoquinoline, 1,2-dihydroquinoline, purine and like rings.

The term "electron-donating group," as used herein, means a functional group which releases electrons to itself more than a hydrogen atom would at the same position. Exemplary electron-donating groups include —OH, —SH, $-NH_2$ and the like.

As used herein, "indicating group" means a functional group indicating the presence of the anion to be tested or the quantity thereof. In other words, the indicating group means a functional group that generates a detectable signal depending on the quantity of the anion to be tested. "Chromogenic group" means a functional group that generates an optical signal such as color change accompanied by the change of electronic density (or configuration), which is easily detected by eye or absorbance spectrum. "Fluorescent group" means a functional group that changes fluorescence quantum yield accompanied by the change of electronic density (or configuration), and "electrochemical group"

means a functional group that generates an electrical signal accompanied by the change of electronic density (or configuration).

The term "alkyl" as used herein is intended to include both "unsubstituted alkyls" and "substituted alkyls," the latter of which refers to alkyl moieties having substituents replacing a hydrogen on one or more carbons of the hydrocarbon backbone. Such substituents can include, for example, a halogen, a hydroxyl, an alkenyl, an alkynyl, a carbonyl, an alkoxyl, an ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides and silyl groups, as well as ethers, thioethers, selenoethers, carbonyls (including ketones, aldehydes, carboxylates, and esters), —$CF_3$, —CN and the like. Preferable is a straight or branched saturated carbon chain having from one to six carbon atoms. Examples include methyl, ethyl, n-propyl, isopropyl, n-butyl, sec-butyl, isobutyl, t-butyl, n-pentyl, sec-pentyl, isopentyl, n-hexyl. "Alkylene" means alkyl with two points of attachment; examples include methylene, ethylene, and propylene. "Alkenyl" means a straight or branched carbon chain having at least one carbon-carbon double bond, and having from two to six carbon atoms. Examples include ethenyl, propenyl, isopropenyl, butenyl, isobutenyl, pentenyl, and hexenyl. "Alkynyl" means a straight or branched carbon chain having at least one carbon-carbon triple bond, and from two to six carbon atoms. Examples include ethynyl, propynyl, butynyl, and hexynyl.

As used herein, "amino" means —$NH_2$, "nitro" means —$NO_2$, "halogen" means —F, —Cl, —Br or —I, "hydroxyl" means —OH, "thiol" means —SH, "alkoxy" means —OR(R: alkyl), "thioalkyl" means —SR(R: alkyl) and "carboxyl" means —COOH, and "alkylamine" means an alkyl group, as defined above, having a substituted or unsubstituted amine attached hereto.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds, illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

"Heteroaryl" or "heteroaromatic ring," as used herein, means a aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, quinolinyl purinyl, and like rings.

Besides the terms defined in the above, the terminology cited herein would be readily understood by ordinary person in an art to which the present invention pertains.

II. Sensors

According to a first aspect of the present invention, a coordination complex formed by dinuclear metal complexation is provided. The coordination complex is a dinuclear metal complex of a compound, wherein the compound comprises a conjugation ring system substituted with: a) an electron donating group selected from —OH, —SH and —$NH_2$; b) an indicating group selected from a chromogenic group, a fluorescent group and an electrochemical group; and c) two binding auxiliary groups, in combination with the electron donating group each of which being coordinated with the metal to provide an anion bonding site. Preferably, the anion is pyrophosphate.

As for the conjugation ring system, an aromatic ring system can be mentioned. The aromatic ring system includes a hydrocarbon aromatic ring system and a hetero-aromatic ring system bearing at least one and up to four non-carbon atoms selected from oxygen, sulfur and nitrogen. As a hydrocarbon aromatic ring system, an aryl ring system such as benzene, indene, naphthalene, anthracene, phenanthrene and the likes can be mentioned. As a hetero-aromatic ring system, thiophene, furan, pyrrole, imidazole, pyrazole, thiazole, isothiazole, oxazole, isoxazole, triazole, thiadiazole, oxadiazole, tetrazole, thiatriazole, oxatriazole, pyridine, pyrimidine, pyrazine, pyridazine, triazine, tetrazine, quinoline, isoquinoline, 1,2-dihydroquinoline, purine and like rings can be mentioned.

The chromogenic group is not particularly limited. The chromogenic group which has been widely used in a field of, for example, analysis or screening can be used. Representative examples of the chromogenic group are azo-compounds. According to specific embodiment of the present invention, p-nitrophenylazo group was used as a chromogenic group, and which gave an eye-detectable color change in an aqueous medium and accurate quantification of the pyrophosphate anion in absorption test. Specific Examples of the fluorescent group include naphthyl group, anthracenoyl group and DCM derivatives such as 4-dicyanometylene-2-methly-6-[p-(dimethylamino)styryl]-4H-pyran)-2'-bis-(amino-methyl)biphen, pyren and porphyrin. Specific Examples of the electrochemical group include ferrocenoyl-ethylene moieties, furyl moieties, thienyl moieties.

The metals used for complex formation are not particularly limited. Regarding substituents present on the conjugation ring system, the metals can be suitably selected. According to a specific embodiment of the present invention, various metal ions including $Zn^{2+}$, $Fe^{2+}$, $Fe^{3+}$, $Mn^{2+}$, $Mn^{3+}$, $Cu^{2+}$, $Co^{2+}$, $Co^{3+}$, $Hg^{2+}$, $Pb^{2+}$, $Ce^{2+}$, $Cd^{2+}$ and $Mg^{2+}$ were tested in terms of the selectivity and the sensitivity for pyrophosphate anion. $Zn^{2+}$, $Co^{3+}$, $Cd^{2+}$, $Fe^{3+}$, and $Cu^{2+}$ ions were proven to be particularly suitable for the pyrophosphate assay. Most preferable was $Zn^{2+}$.

Each of the two binding auxiliary groups contains at least one atom having an unshared electron pair, for example oxygen, nitrogen and sulfur. They were coordinated with the metals, in combination with oxygen atom, nitrogen atom or sulfur atom of the electron donating group. For example, when the conjugation ring system and the electron donating group are a benzene ring system and a hydroxyl group respectively, a phenoxo-bridged dinuclear metal complex is formed. In the case that thiol or amine group instead of the hydroxyl group is used as an electron donating group, similar dinuclear metal complex will be formed. When the complex is added to a sample in which an anion is to be assayed is present, the complex binds to the anion. At this time, the binding auxiliary groups, each of which being coordinated with a metal ion, provide an anion bonding site.

According to X-ray analysis, it was revealed that as the complex binds to the anion, the coordination of the electron donating group with the metal is weakened. This induces more negative charge character on the electron donating group. The induced negative charge character reinforces electron donation of the electron donating group to the conjugation ring system, and the reinforced electron donation is transferred through the conjugation ring system to the indicating group substituted with the system. Particularly, when the indicating group is substituted at para position on a benzene ring system, the effect of the electron donation by the electron donating group is maximized. As a result, the electron density of the indicating group is highly increased. Such an increase produces a detectable indicating signal such as color change, fluorescence quantum yield change or electron release.

According to the preferred embodiment of the present invention, a dinuclear metal complex of a compound having formula I was particularly suitable:

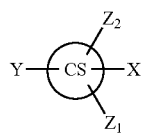

(I)

wherein, X is an electron donating group selected from —OH, —SH and —NH$_2$; Y is an indicating group selected from a chromogenic group, a fluorescent group and an electrochemical group; Z$_1$ and Z$_2$ are binding auxiliary groups, both of which are each independently hydrocarbons containing at least one atom selected from the group consisting of N, O, S and P; and

is a conjugation ring system. Preferred example of the conjugation system is aromatic ring system in which each of the two binding auxiliary groups are substituted at an ortho position and the indicating group is at a para position relative to the electron donating group. Each of the two binding auxiliary groups contains at least one atom having an unshared electron pair such as oxygen, nitrogen and sulfur. The binding auxiliary group complexed with the metal provides an anion binding site.

Preferably, the complex is a dinuclear metal complex of the compound having formula II:

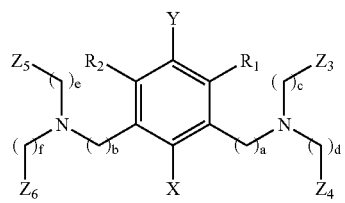

(II)

wherein, X is an electron donating group selected from —OH, —SH and —NH$_2$; Y is an indicating group selected from a chromogenic group, a fluorescent group and an electrochemical group; Z$_3$, Z$_4$, Z$_5$ and Z$_6$ are each independently hydrocarbons containing at least one atom selected from the group consisting of N, O, S and P; R$_1$ and R$_2$ are each independently selected from the group consisting of hydrogen, halogen, hydroxyl, amino, alkyl, alkoxy, thioalkyl, alkylamino, imine, amide, phosphate, phosphine, carbonyl, carboxyl, silyl, ether, thioether, sulfonyl, selenoether and ketone; and a, b, c, d, e and f are each independently integers of 1 to 3, more preferably 1 or 2. Specific examples of Z$_3$, Z$_4$, Z$_5$ and Z$_6$ are each independently —NR$_3$R$_4$, —OR$_5$, —SR$_6$, —PR$_7$R$_8$, a hetero aliphatic cycle and a heteroaromatic ring, wherein R$_3$, R$_4$,R$_5$, R$_6$, R$_7$, and R$_8$ are each independently an alkyl or a substituted alkyl. Preferably, Z$_3$, Z$_4$, Z$_5$ and Z$_6$ are each independently heteroaromatic ring having a formula:

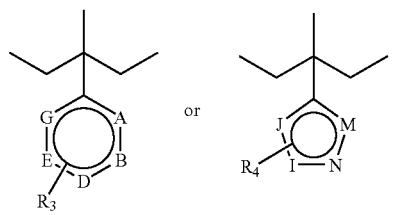

wherein, at least one of A, B, D, E and G is nitrogen, and the others are oxygen or carbon, and at least one of I, J, M and N is oxygen and the others are nitrogen or carbon. R$_3$ and R$_4$ are each independently selected from the group consisting of a hydrogen, a halogen, a hydroxyl, an amino, an alkyl, an alkoxy, a thioalkyl, an alkylamino, an imine, an amide, a phosphate, a phosphine, a carbonyl, a carboxyl, a silyl, an ether, a thioether, a sulfonyl, a selenoether and a ketone. Specific examples of the heteroaromatic ring include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, quinolinyl purinyl, and the likes. They may be substituted, preferably, with a substituent which provides a binding site to form a self assembled monolayer. For example, a carboxyl group can be mentioned. Fixation to a solid phase is well known in the art. Please refer to the following documents: John J. Lavigne and Eric V. Anslyn, Angew. Chem. Int. Ed. 2001, 40, 3118-3130; Abraham Ulman, Chem. Rev. 1996, 96, 1533-1554; Mercedes Crego-Calama and David N. Reinhoudt, Adv. Mater. 2001, 13, No. 15, 1171-1174; Victor Chechik, Richard M. Crooks, and Charles J. M. Stirling, Adv. Mater. 2000, 12, No. 16, 1161-1171; Simon Flink, Frank C. J. M. van Veggel, and David N. Reinhoudt, Adv. Mater. 2000, 12, No. 18, 1315-1328.

III. EXAMPLES

A. Synthesis of p-(p-nitrophenylazo)-bis[(bis(2-pyridylmethyl)amino)methyl]phenol and its dinuclear Zn complex.

P-(p-nitrophenylazo)-bis[(bis(2-pyridylmethyl)amino) methyl]phenol (hereinafter, "compound 1) and its dinuclear Zn complex was synthesized according to scheme I:

SCHEME I

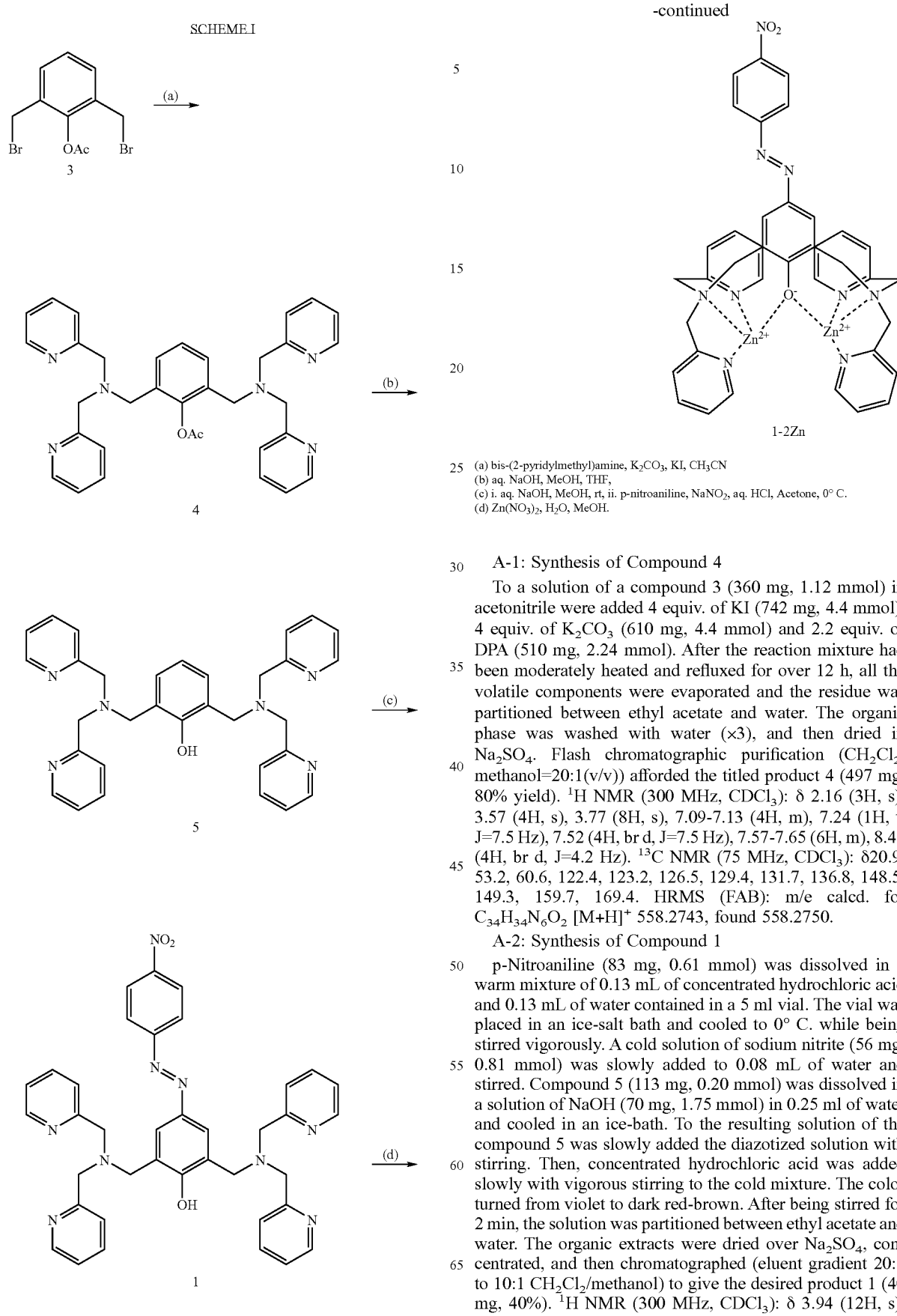

(a) bis-(2-pyridylmethyl)amine, K$_2$CO$_3$, KI, CH$_3$CN
(b) aq. NaOH, MeOH, THF,
(c) i. aq. NaOH, MeOH, rt, ii. p-nitroaniline, NaNO$_2$, aq. HCl, Acetone, 0° C.
(d) Zn(NO$_3$)$_2$, H$_2$O, MeOH.

A-1: Synthesis of Compound 4

To a solution of a compound 3 (360 mg, 1.12 mmol) in acetonitrile were added 4 equiv. of KI (742 mg, 4.4 mmol), 4 equiv. of K$_2$CO$_3$ (610 mg, 4.4 mmol) and 2.2 equiv. of DPA (510 mg, 2.24 mmol). After the reaction mixture had been moderately heated and refluxed for over 12 h, all the volatile components were evaporated and the residue was partitioned between ethyl acetate and water. The organic phase was washed with water (×3), and then dried in Na$_2$SO$_4$. Flash chromatographic purification (CH$_2$Cl$_2$: methanol=20:1(v/v)) afforded the titled product 4 (497 mg, 80% yield). $^1$H NMR (300 MHz, CDCl$_3$): δ 2.16 (3H, s), 3.57 (4H, s), 3.77 (8H, s), 7.09-7.13 (4H, m), 7.24 (1H, t, J=7.5 Hz), 7.52 (4H, br d, J=7.5 Hz), 7.57-7.65 (6H, m), 8.49 (4H, br d, J=4.2 Hz). $^{13}$C NMR (75 MHz, CDCl$_3$): δ20.9, 53.2, 60.6, 122.4, 123.2, 126.5, 129.4, 131.7, 136.8, 148.5, 149.3, 159.7, 169.4. HRMS (FAB): m/e calcd. for C$_{34}$H$_{34}$N$_6$O$_2$ [M+H]$^+$ 558.2743, found 558.2750.

A-2: Synthesis of Compound 1 p-Nitroaniline (83 mg, 0.61 mmol) was dissolved in a warm mixture of 0.13 mL of concentrated hydrochloric acid and 0.13 mL of water contained in a 5 ml vial. The vial was placed in an ice-salt bath and cooled to 0° C. while being stirred vigorously. A cold solution of sodium nitrite (56 mg, 0.81 mmol) was slowly added to 0.08 mL of water and stirred. Compound 5 (113 mg, 0.20 mmol) was dissolved in a solution of NaOH (70 mg, 1.75 mmol) in 0.25 ml of water and cooled in an ice-bath. To the resulting solution of the compound 5 was slowly added the diazotized solution with stirring. Then, concentrated hydrochloric acid was added slowly with vigorous stirring to the cold mixture. The color turned from violet to dark red-brown. After being stirred for 2 min, the solution was partitioned between ethyl acetate and water. The organic extracts were dried over Na$_2$SO$_4$, concentrated, and then chromatographed (eluent gradient 20:1 to 10:1 CH$_2$Cl$_2$/methanol) to give the desired product 1 (40 mg, 40%). $^1$H NMR (300 MHz, CDCl$_3$): δ 3.94 (12H, s), 7.23 (4H, dd, J=5.1, 6.6 Hz), 7.56 (4H, br d, J=7.8 Hz), 7.68-7.75 (4H, m), 8.01 (2H, s), 8.03 (2H, d, J=12 Hz), 8.41 (2H, d, J=12 Hz), 8.53 (4H, d, J=4.5 Hz). $^{13}$C NMR (75 MHz, CDCl$_3$): δ 54.5, 59.7, 122.5, 123.2, 123.3, 125.1, 125.6, 125.9, 126.2, 136.9, 145.6, 148.5, 149.2, 156.5, 159.4, 161.4, MS (ESI): m/e calcd. for C$_{38}$H$_{35}$N$_9$O$_3$ [M+H]$^+$ 666.3, found [M+H]$^+$ 666.9. Anal Calcd for C$_{38}$H$_{35}$N$_9$O$_3$: C, 68.56; H, 5.30; N, 18.94. found: C, 67.16; H, 5.31; N, 17.85.

A-3: Synthesis of Dinuclear Zn Metal Complex of the Compound 1 ("1•2Zn")

To a solution of 1 (100 mg, 0.15 mmol) in 20 mL of MeOH, was added dropwise aqueous solution of Zn(NO$_3$)$_2$·6H$_2$O(0.5 M; 0.65 mL, 0.32 mmol), and the mixture was stirred for 30 min at rt. After concentrating in vacuo, the aqueous solution was lyophilized. The obtained solid was recrystallized from MeOH-water (1:1) to give a sensor 1•2Zn (70 mg, 45%). $^1$H NMR (300 MHz, MeOH-d$_4$ +D$_2$O): δ 3.78 (4H, s), 4.18 (8H, dd, J=15.6, 45 Hz), 7.23 (4H, br s), 7.39 (4H, br s), 7.45 (4H, br s), 7.70 (4H, br s), 7.87 (4H, d, J=9 Hz), 8.36 (4H, d, J=9 Hz), 8.50 (4H, br s). MALDI-TOF-MS: m/e calcd. for C$_{38}$H$_{34}$N$_{11}$O$_9$·2Zn·2NO$_3$ [M]$^+$ 916.11. found 916.84. Anal Calcd for C$_{38}$H$_{34}$N$_{11}$O$_9$·2Zn·3NO$_3$·2H$_2$O: C, 44.85; H, 3.76; N, 16.52. found: C, 43.16; H, 3.55; N, 16.60

For comparison, p-(p-nitrophenylazo)-[(bis(2-pyridylmethyl)amino)methyl]phenol (hereinafter, "compound 2") and a 1:1 Zn metal complex of the compound 2 were synthesized according to scheme II:

SCHEME II

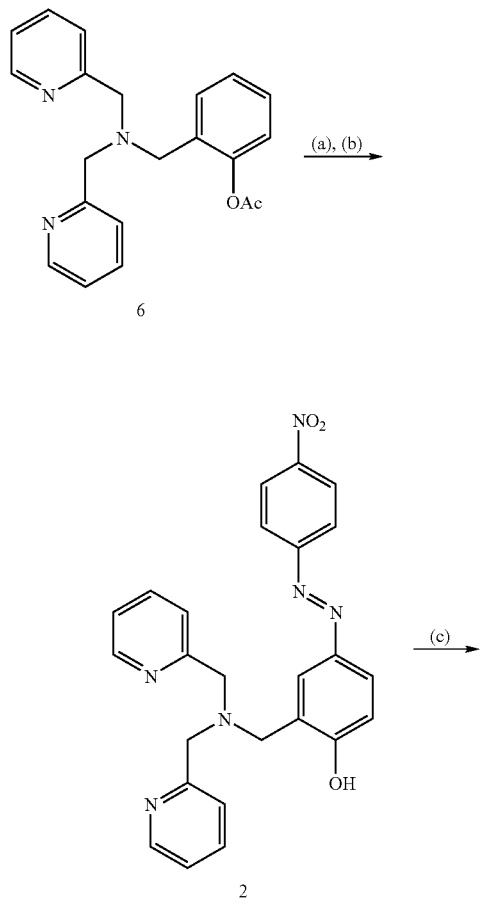

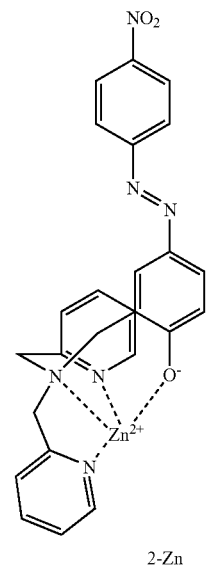

(a) aq. NaOH, MeOH, THF,
(b) i. aq. NaOH, MeOH, rt, ii. p-nitroaniline, NaNO$_2$, aq. HCl, Acetone, 0° C.
(c) Zn(NO$_3$)$_2$, H$_2$O, MeOH.

A'-1: Synthesis of Compound 6

By the same procedure described in the synthesis of the compound 4, compound 6 (232 mg, 80%) was obtained: $^1$H NMR (300 MHz, Acetone-d$_6$): δ 2.24 (3H, s), 3.67 (2H, s), 3.76 (4H, s), 7.05 (1H, dd, J=3.2, 6.6 Hz), 7.21-7.28 (4H, m), 7.62 (2H, d, J=7.8 Hz), 7.72-7.77 (3H, m), 8.51 (2H, d, J=4.2 Hz). HRMS (FAB): m/e calcd. for C$_{21}$H$_{21}$N$_3$O$_2$ [M+H]$^+$ 348.1634, found [M+H]$^+$ 348.1785.

A'-2: Synthesis of Compound 2

Compound 6 (100 mg, 0.29 mmol) was used as a starting material. By the same procedure described for the synthesis of compound 1, compound 2 (68 mg, 52%) was obtained.: $^1$H NMR (300 MHz, Acetone-d$_6$): δ 3.98 (6H, s), 7.05 (1H, d, J=9.3 Hz), 7.30-7.33 (2H, m), 7.45 (2H, d, J=7.8 Hz), 7.77 (2H, dd, J=1.8, 7.8 Hz), 7.91-7.94 (2H, m), 8.07 (2H, d, J=9.0 Hz), 8.44 (2H, d, J=9.0 Hz), 8.59 (2H, d, J=4.8 Hz). $^{13}$C NMR (75 MHz, CDCl$_3$): δ 56.1, 52.9, 54.9, 113.9, 119.1, 119.4, 119.7, 120.1, 121.1, 122.2, 122.7, 133.9, 142.1, 144.3, 144.7, 152.6, 154.1, 158.6. HRMS (FAB): m/e calcd. for C$_{25}$H$_{22}$N$_6$O$_3$ [M+H]$^+$ 455.1832, found 455.1850. Anal Calcd for C$_{25}$H$_{22}$N$_6$O$_3$: C, 66.07; H, 4.88; N, 18.49. found: C, 65.20; H, 4.96; N, 17.63.

A'-3: Synthesis of 1:1 Zn Metal Complex of the Compound 2

Compound 2 (50 mg, 0.11 mmol) was used as a starting material. By the same procedure described for the synthesis of sensor 1•2Zn, 1:1 Zn metal complex of the compound 2 (hereinafter "2•Zn") (39 mg, 55%) was obtained. $^1$H NMR (300 MHz, Acetone-d$_6$): δ3.96 (2H, s), 4.39 (4H, d, J=3.6 Hz), 6.60 (1H, br s), 7.66-7.73 (5H, m), 7.79 (1H, s), 7.96 (2H, d, J=8.7 Hz), 8.14 (2H, t, J=7.8 Hz ), 8.38 (2H, d, J=8.7 Hz), 8.78 (2H, d, J=5.4 Hz). MS (ESI): m/e calcd. for C$_{25}$H$_{21}$N$_6$O$_3$·Zn [M]$^+$ 517.1, found 517.6. Anal Calcd for C$_{25}$H$_{21}$N$_6$O$_3$·Zn·NO$_3$·H$_2$O: C, 50.14; H, 3.87; N, 16.37. found: 49.94; H, 3.77; N, 16.42

B. Synthesis of p-naphthyl-bis[(bis(2-pyridylmethyl)amino)methyl]phenol and its dinuclear Zn complex p-naphthyl-bis[(bis(2-pyridylmethyl)amino)methyl]phenol (hereinafter, "compound 7") was synthesized according to scheme III:

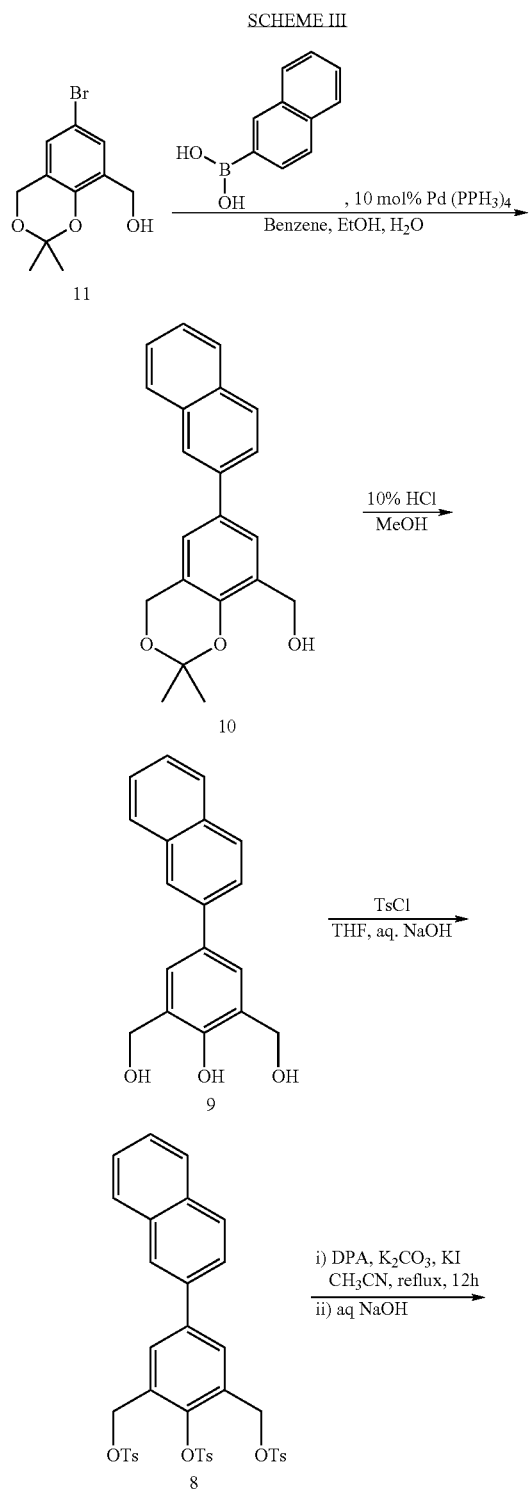

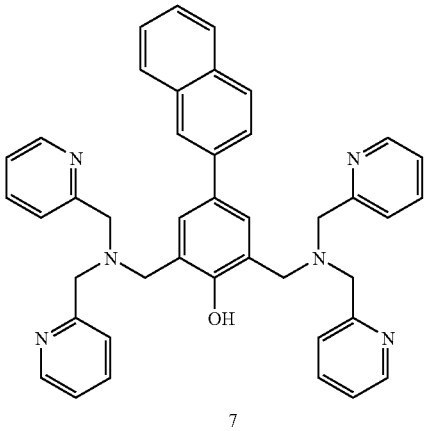

B-1: Synthesis of Compound 10

To a solution of compound 11 (500 mg, 1.83 mmol) and tetrakistriphenylphosphine)palladium(0) (113 mg, 0.09 mmol) in 9 mL of benzene under argon was added 4.0 mL of 2 N aq. sodium carbonate followed by 2-naphthaleneboronic acid (630 mg, 3.66 mmol) in 4 µL of EtOH. The mixture was refluxed for 16 h, diluted with 50 mL of water and extracted with 3×50 mL of EtOAc. The combined organic extracts were washed once with 50 mL of brine, dried and evaporated. The residue was chromatographed on silica gel using hexanes/EtOAc (3:1) to afford compound 10 (563 mg, 96% yield). $^1$H NMR (300 MHz, Acetone-$d_6$): δ 1.56 (6H, s), 4.76-4.78 (2H, d, J=6.0 Hz), 4.96 (2H, s), 7.40 (1H, s), 7.47-7.52 (2H, m), 7.81-7.95 (5H, m), 8.12 (1H, s). $^{13}$C NMR (75 MHz, CDCl$_3$): δ 024.7, 59.9, 61.0, 100.1, 119.9, 122.3, 125.0, 125.1, 125.6, 126.1, 126.7, 128.0, 128.5, 128.8, 130.9, 132.8, 132.9, 134.4, 138.7, 148.5.

B-2: Synthesis of Compound 9

To a stirred solution of compound 10 (320 mg, 1.0 mmol) in 10 mL MeOH was added 5 mL of 10% HCl. The reaction mixture was stirred at room temperature for 12 h, and then all the volatile components were evaporated and the residue was partitioned between ethyl acetate and water. The organic phase was washed with water (×3), and then dried in Na$_2$SO$_4$. This solution was evaporated under reduced pressure to leave the residue, which was triturated with hexane. When white solids were precipitated, the precipitates were filtered, washed with hexane, and dried in vacuo to afford compound 9 (252 mg, 90% yield). $^1$H NMR (300 MHz, Acetone-$d_6$): δ 4.91 (4H, s), 7.44-7.53 (2H, m), 7.64 (2H, s), 7.81 (1H, d, J=9.0 Hz), 7.88-7.95 (3H, m), 8.11 (1H, s). $^{13}$C NMR (75 MHz, CDCl$_3$): δ 861.8, 124.8, 125.3, 125.6, 125.9, 126.6, 127.9, 128.0, 128.4, 128.7, 132.0, 132.8, 134.4, 138.8, 154.0.

B-3: Synthesis of Compound 8

To a stirred solution of compound 9 (252 mg, 0.9 mmol) in 10 mL of THF was added 10 mL of 0.5 N aq. NaOH solution at 0° C. To the resulting solution was added para-toluenesulfonyl chloride (532 mg, 2.79 mmol) dissolved in 10 mL of THF. The reaction mixture was stirred at 0° C. for 4 h, and then all the volatile components were evaporated and the residue was partitioned between ethyl acetate and water. The organic phase was washed with water (×3), and then dried in Na$_2$SO$_4$. Flash chromatographic purification (Hexane: EtOAc=3:1(v/v)) afforded compound 8 (334 mg, 50% yield). $^1$H NMR (300 MHz, Acetone-$d_6$): δ 2.07 (6H, s), 2.39 (3H, s), 5.13 (4H, s), 7.42 (4H, d, J=9.0 Hz), 7.57-7.60 (4H, m), 7.69 (1H, d, J=9.0 Hz), 7.75-7.83 (8H, m), 7.97 (1H, d, J=9.0 Hz), 8.05 (2H, d, J=8.7 Hz), 8.10 (1H, s).

B-4: Synthesis of Compound 7

To a solution of 8 (334 mg, 0.45 mmol) in acetonitrile were added 4 equiv. of KI (298 mg, 1.8 mmol), 4 equiv. of $K_2CO_3$ (248 mg, 1.8 mmol) and 2.2 equiv. of DPA (197 mg, 0.99 mmol). The reaction mixture had been moderately heated and refluxed for over 12 h. After insoluble inorganic salts were removed by filtration, all the volatile components were evaporated. The resulting residue was dissolved in 10 mL MeOH. To the stirred solution was added 5 mL of 2N aq. NaOH for hydrolysis. The reaction mixture was stirred at room temperature for 2 h. The mixture was neutralized with 1N HCl and partitioned between ethyl acetate and water. The organic phase was washed with water (×3), and then dried in $Na_2SO_4$. Flash chromatographic purification ($CH_2Cl_2$: methanol=20:1(v/v)) afforded 7 (231 mg, 80% yield).

$^1$H NMR (300 MHz, Acetone-$d_6$): δ 3.94 (12H, s), 7.21 (4H, t, J=5.7 Hz), 7.48 (2H, m), 7.61 (4H, d, J=7.8 Hz), 7.71 (4H, t, J=7.2 Hz), 7.78 (2H, s), 7.85-7.96 (4H, m), 8.54 (1H, s), 8.54 (4H, d, J=3.9 Hz). $^{13}$C NMR (75 MHz, $CDCl_3$): δ 54.8, 59.8, 122.5, 123.2, 124.7, 125.1, 125.7, 125.8, 126.3, 126.6, 127.9, 128.4, 128.7, 130.9, 132.7, 134.4, 136.9, 138.9, 149.3, 156.6, 159.8. HRMS (FAB): m/e calcd. for $C_{42}H_{38}N_6O$ [M+H]$^+$ 643.3107, found 643.3185.

B-5: Synthesis of a Dinuclear Zn Metal Complex of the Compound 7 ("7•2Zn")

To a solution of 7 (64 mg, 0.10 mmol) in 20 μL of MeOH, was added dropwise aqueous solution of $Zn(NO_3)_2.6H_2O$ (0.5 M; 0.42 mL, 0.21 mmol), and the mixture was stirred for 30 min at room temperature. After concentrating in vacuo, the aqueous solution was lyophilized. The obtained solid was recrystallized from MeOH-water (1:1) to give a sensor 7•2Zn (48 mg, 48% yield).

$^1$H NMR (300 MHz, acetone-$d_6$): δ 4.16 (4H, s), 4.45 (8H, dd, J=18, 54 Hz), 7.41 (2H, br s), 7.47-7.54 (9H, m), 7.62 (2H, d, J=12 Hz), 7.89-7.93 (4H, m), 7.98 (4H, br s), 8.62 (4H, br)

C. Synthesis of ferrocenoylethynylene-bis[bis(2-pyridylmethyl)amino)methyl]phenol and its dinuclear Zn complex Ferrocenoylethynylene-bis[bis(2-pyridylmethyl)amino) methyl]phenol (hereinafter, "compound 12") was synthesized according to scheme IV:

SCHEME IV

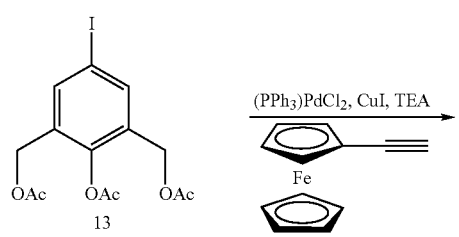

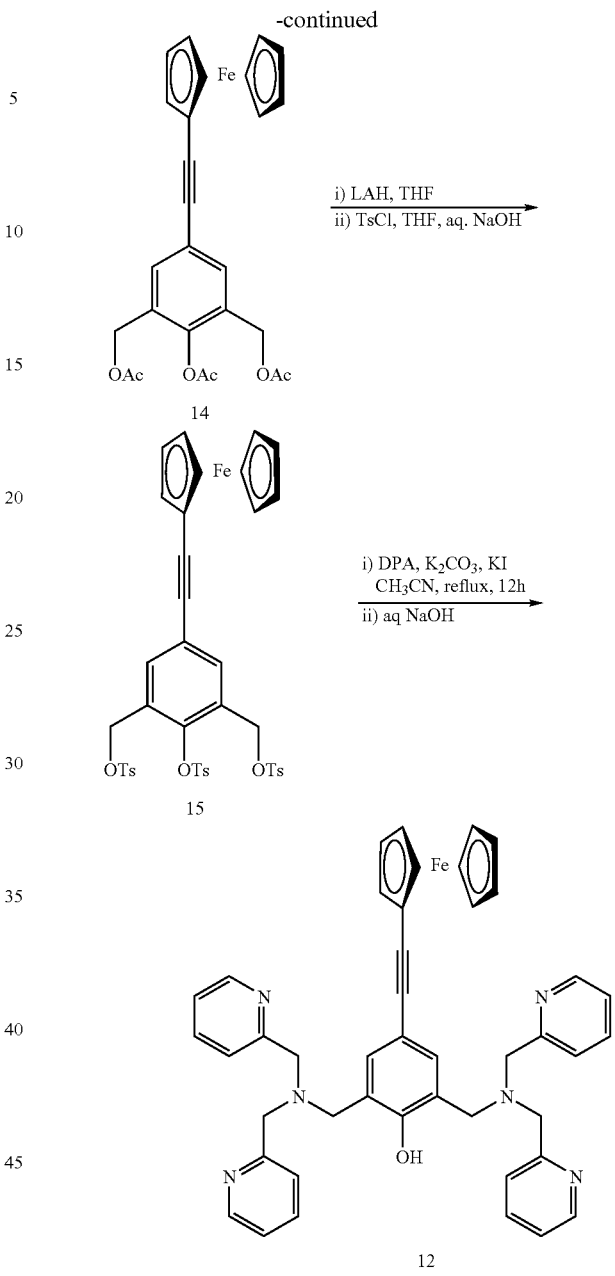

C-1: Synthesis of Compound 14

To a solution of a compound 13 (400 mg, 0.98 mmol), (dichloridebistriphenylphosphine)palladium(0) (72 mg, 0.1 mmol), cupper iodide (38 mg, 0.2 mmol), triphenylphosphine (75 mg, 0.29 mmol) and ferrocenoylethynylene (256 mg, 1.2 mmol) in 10 mL of methylene chloride was added 5.0 mL of triethylamine solution under argon atmosphere. The mixture was refluxed for 1 h, diluted with 50 mL of water and extracted with 3×50 mL of EtOAc. The combined organic extracts were washed with 50 mL of brine, dried and evaporated. The residue was chromatographed on silica gel using hexanes/EtOAc (4:1) to afford compound 14 (455 mg, 95% yield).

$^1$H NMR (300 MHz, acetone-$d_6$): δ 2.07 (6H, s), 2.37 (3H, s), 4.27 (5H, s), 4.33-4.34 (2H, m), 4.55-4.56 (2H, m), 5.06 (4H, s), 7.59 (2H, s).

C-2: Synthesis of Compound 15

The compound 14 (455 mg, 0.94 mmol) was dissolved in 20 mL of tetrahydrofuran and then cooled to 0° C. To the solution, lithiumaluminiumhydride (71 mg, 1.88 mmol) was added and stirred for 10 min at 0° C. Water and 15% NaOH solution were added to complete the reaction. After further stirring for 10 min at room temperature, 10 mL of water and NaOH (376 mg, 9.4 mmol) was added and stirred for 30 min at 0° C. To the obtained solution, para-toluenesulfonyl chloride (1064 mg, 5.58 mmol) in 10 mL of THF was added. The reaction mixture was stirred for 4 h at 0° C., and then all the volatile components were evaporated. The resulting residue was partitioned between ethyl acetate and water. The organic phase was washed with water (×3), and then dried in $Na_2SO_4$. Flash chromatographic purification (Hexane: ethylacetate=3:1(v/v)) afforded 15 (327 mg, 40% yield).

$^1H$ NMR (300 MHz, acetone-$d_6$): δ 2.46(s, 6H), 2.53(s, 3H), 4.28(s, 5H), 4.35(d, J=3 Hz, 2H), 4.58(d, J=3 Hz, 2H), 4.99(s, 4H), 7.45-7.48(m, 6H), 7.55(d, J=6 Hz, 2H), 7.56□7.80(m, 6H). $^{13}C$ NMR (75 MHz, acetone-$d_6$): δ 14.00, (21.16), 21.26, (21.41), 22.86, 31.85, (64.40), 66.34, 69.76, 70.25, 70.39, 71.92, 83.59, 91.59, 124.21, 128.26, 128.69, 130.12, 130.54, 131.06, 131.77, 133.34, 133.84, 143.50, 145.80, 147.62.

C-3: Synthesis of Compound 12

To a solution of the compound 15 (327 mg, 0.40 mmol) in acetonitrile were added 4 equiv. of KI (264 mg, 1.6 mmol), 4 equiv. of $K_2CO_3$ (220 mg, 1.6 mmol) and 2.2 equiv. of DPA (160 mg, 0.80 mmol). The reaction mixture had been moderately heated and refluxed for over 12 h. After insoluble inorganic salts were removed by filtration, all the volatile components were evaporated. The resulting residue was dissolved in 10 mL MeOH. To the stirred solution was added 5 mL of 2N aq. NaOH for hydrolysis. The reaction mixture was stirred at room temperature for 2 h. The mixture was neutralized with 1N HCl and partitioned between ethyl acetate and water. The organic phase was washed with water (×3), and then dried in $Na_2SO_4$. Flash chromatographic purification ($CH_2Cl_2$: methanol=20:1(v/v)) afforded 12 (230 mg, 80% yield).

$^1H$ NMR (300 MHz, acetone-$d_6$): δ 3.83(s, 4H), 3.89(s, 8H), 4.23(s, 5H), 4.24(s, 2H), 4.47(s, 2H), 7.24(d, J=6 Hz), 7.44(s, 2H), 7.57(d, J=9 Hz, 4H), 7.72(t, J=9 Hz, 4H), 8.53(d, J=6 Hz, 4H), $^{13}C$ NMR (75 MHz, acetone-$d_6$): δ 13.97, 22.85, 31.85, 54.39, 59.63, (66.49), 68.99, 70.19, 71.46, 85.95, 86.58, 113.77, 122.53, 123.18, 125.19, 132.90, 136.99, 149.23, 156.96, 159.60.

C-4: Synthesis of a Dinuclear Zn Metal Complex of the Compound 12 ("12•2Zn")

To a solution of 12 (74 mg, 0.10 mmol) in 20 mL of MeOH, was added dropwise aqueous solution of $Zn(NO_3)_2$.$6H_2O$(0.5 M; 0.42 mL, 0.21 mmol), and the mixture was stirred for 30 min at room temperature. After concentrating in vacuo, the aqueous solution was lyophilized. The obtained solid was recrystallized from MeOH-water (1:1) to give a sensor 12•2Zn (43 mg, 50% yield).

$^1H$ NMR (300 MHz, MeOH-$d_4$+$D_2O$): δ 3.88 (4H, s), 4.23(s, 5H), 4.32 (8H, dd, J=13.6 40 Hz), 4.42(s, 2H), 4.65(s, 2H), 7.10 (2H, br s), 7.47 (4H, br s), 7.70 (4H, br s), 7.87 (4H, br s), 8.50 (4H, br s).

D. Absorption Test of the Dinuclear Metal Complex of the Compound 1

D-1) Effects of the Metals on Absorption Change

First, various metal complexes of the compound 1 were obtained and the effect of the metals on the absorption spectrum was examined. Each of the dinuclear metal complexes was readily obtainable by adding 2 eq. of the corresponding aqueous metal solution to a methanol solution of the compound 1, as shown in zinc complex. The effect of the metals on the absorption spectrum was examined in an aqueous solution of 10 mM HEPES buffer (pH 7.4) (HEPES=2-[4-(2-hydroxy-ethyl)-1-piperazinyl]ethane-sulfonic acid) at 25° C., and each of the anions was used in a form of sodium salt. Specifically, $Zn^{2+}$, $Fe^{2+}$, $Fe^{3+}$, $Mn^{2+}$, $Mn^{3+}$, $Cu^{2+}$, $Co^{2+}$, $Co^{3+}$, $Hg^{2+}$, $Pb^{2+}$, $Ce^{2+}$, $Cd^{2+}$ and $Mg^{2+}$ were used as a metal ion, and selectivity and sensitivity for pyrophosphate anion were tested. UV-visible absorption spectra of $Cu^{2+}$, $Mg^{2+}$, $Pb^{2+}$, $Zn^{2+}$, $Co^{2+}$, $Co^{3+}$, $Hg^{2+}$, $Ce^{2+}$ and $Cd^{2+}$ were summarized in FIG. 1. As shown in FIG. 1, $Zn^{2+}$, $Cd^{2+}$ and $Cu^{2+}$ ions were proven to be particularly suitable for the pyrophosphate assay. $Co^{3+}$ and $Fe^{3+}$ ions gave similar results with that of $Cd^{2+}$ ion. The remaining ions were found to be similar with that of $Mg^{2+}$, $Pb^{2+}$ or $Co^{2+}$.

These results imply that dinuclear metal complexes of $Zn^{2+}$, $Co^{3+}$, $Cd^{2+}$, $Fe^{3+}$ and $Cu^{2+}$ ions are particularly suitable for the pyrophosphate assay. Most preferable is $Zn^{2+}$.

D-2) Absorption Test of the Dinuclear Zn Metal Complex of the Compound 1 ("1•2Zn")

Figure 2:
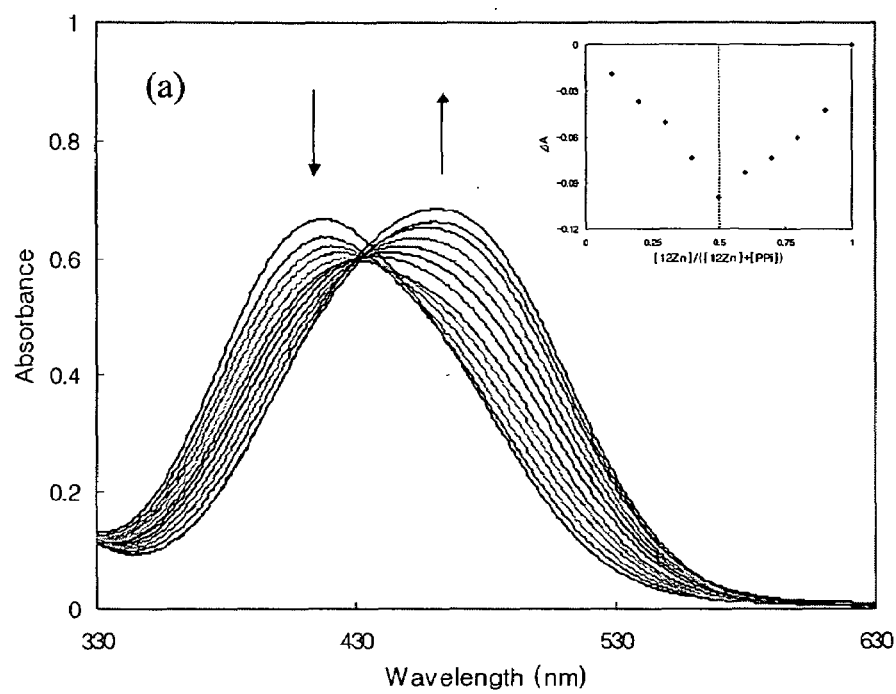
FIG. 2(a) is UV-vis spectra showing absorbance change of sensor 1•2Zn (30 μM) upon addition of PPi (Sodium salt): [PPi]=0, 2, 4, 6, 8, 11, 14, 17, 20, 23, 26, 29, 32 μM. The spectra were measured in an aqueous solvent of 10 mM HEPES buffer (pH 7.4) at 25° C. (Inset) The Job's plot examined between 1•2Zn and PPi.
FIG. 2(b) is UV-vis spectra showing absorbance change of sensor 1•2Zn (30 μM) in pure aqueous solvent 10 mM HEPES buffer (pH 7.4) at 25° C. in the presence of various anions (30 μM).
Figure 2:
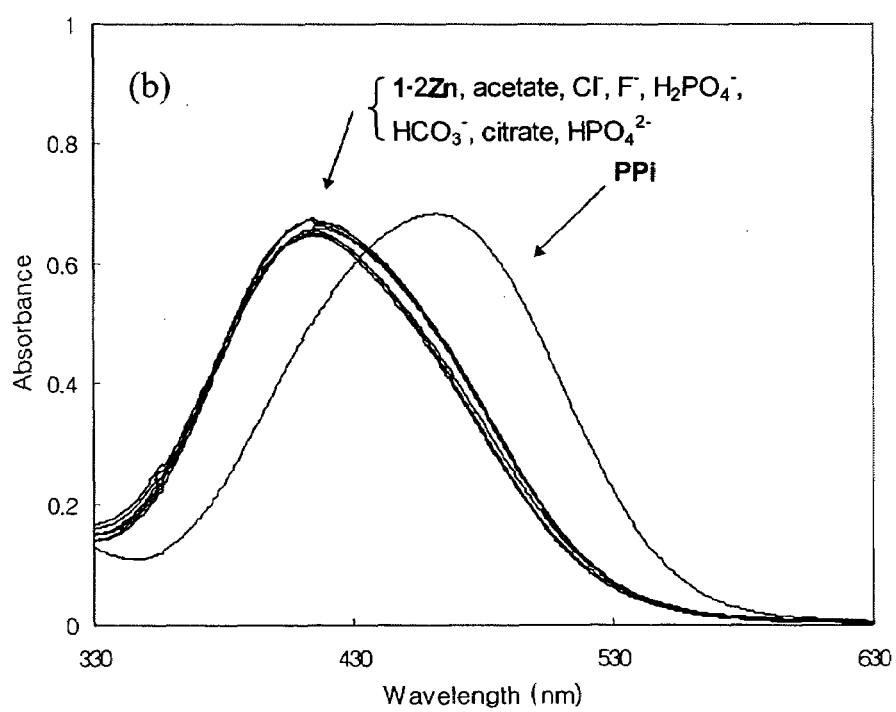

Based on the above results, absorption change of the sensor 1•2Zn was more fully examined. The effect of anions (sodium salts) on the absorption spectrum of 1•2Zn was examined in an aqueous solution of 10 mM HEPES buffer (pH 7.4) at 25° C. (FIG. 2). In the absence of an anion guest, the absorption spectrum of sensor 1•2Zn was characterized by an intense band centered at 417 nm. The optical sensor 1•2Zn did not show any obvious spectral change upon addition of $H_2PO_4^-$ as well as other monovalent anions such as $CH_3CO_2^-$, $F^-$, $HCO_3^-$ and $Cl^-$ even up to an excess of 100 equiv. Moreover, no detectable spectral change was observed upon addition of dibasic anion $HPO_4^{2-}$ and tribasic anion citrate. However, the addition of $P_2O_7^{4-}$ (Ppi) caused bathochromic shifts from 417 nm ($\lambda_{max}$) to 465 nm. It was remarkable that the degree of absorption changes was no longer affected by the addition of more than 1 equiv. of PPi. As shown in UV-vis absorption data of FIG. 6, color change occurred by addition of PPi to the solution of 1•2Zn from yellow to red. Job's plot for the binding between 1•2Zn and PPi showed a 1:1 stoichiometry (inset of FIG. 2(a)). Even in the presence of 10 equiv. of $HPO_4^{2-}$, sensor 1•2Zn showed a similar detection ability for PPi. It was surprising that the apparent association constant, $K_a$, was determined as $(6.6±1.2)×10^8 M^{-1}$ for PPi-1•2Zn by a standard algorithm for competitive binding in the presence of excess $HPO_4^{2-}$ in a pure aqueous solvent of 10 mM HEPES buffer (pH 7.4) at 25° C. These results suggest that sensor 1•2Zn has high selectivity for PPi over other anions.

Figure 3:
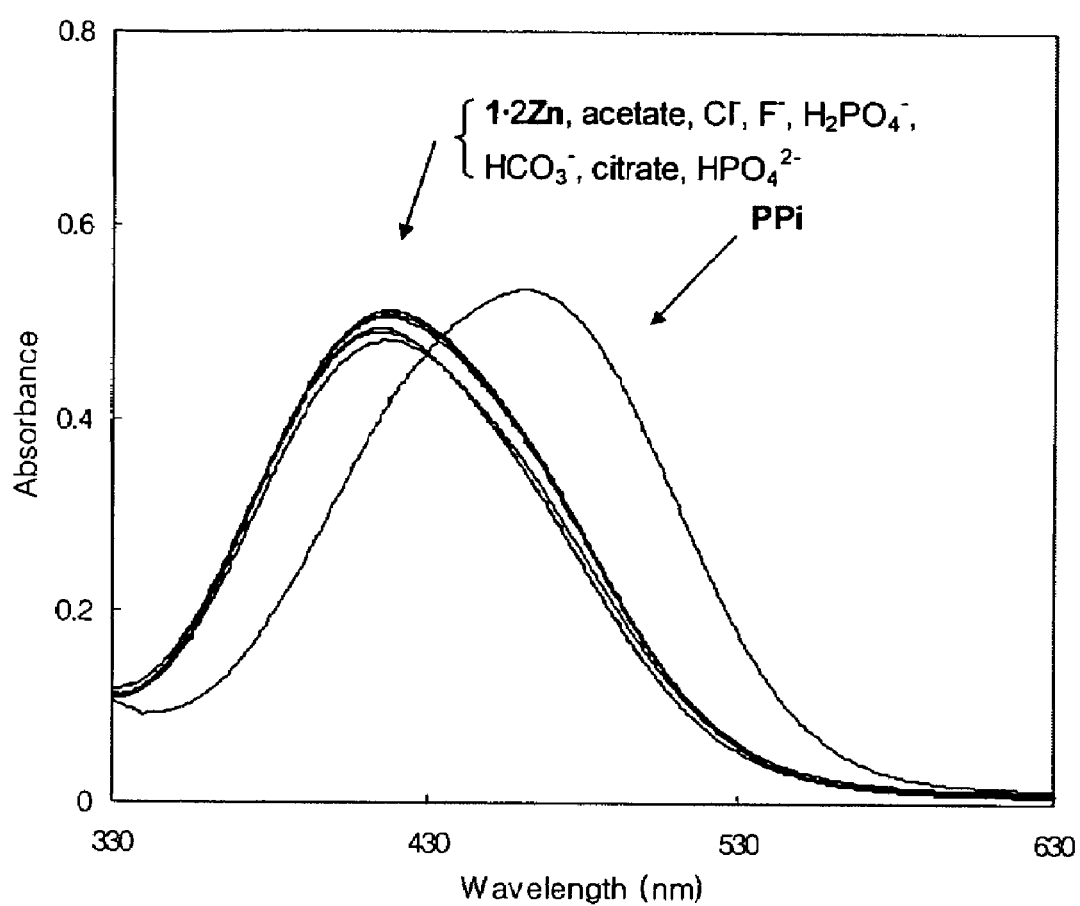
FIG. 3 is UV-vis spectra showing absorbance change of sensor 1•2Zn (30 μM) in pure aqueous solution of 100 mM HEPES buffer (pH 7.4) at 25° C. in the presence of various anions (60 μM).

Similar results were obtained in an aqueous solvent of 100 mM HEPES buffer (pH 7.4) at 25° C. (FIG. 3). The addition of PPi also made a color change from yellow ($\lambda_{max}$=417 nm) to red ($\lambda_{max}$=463 nm). Even in 100 mM HEPES buffer, similar results were observed but sensor 1•2Zn showed the reduced affinity for PPi ($K_a$=(8.3±1.8)×$10^7 M^{-1}$), compared with 10 mM HEPES buffer system.

Figure 4:
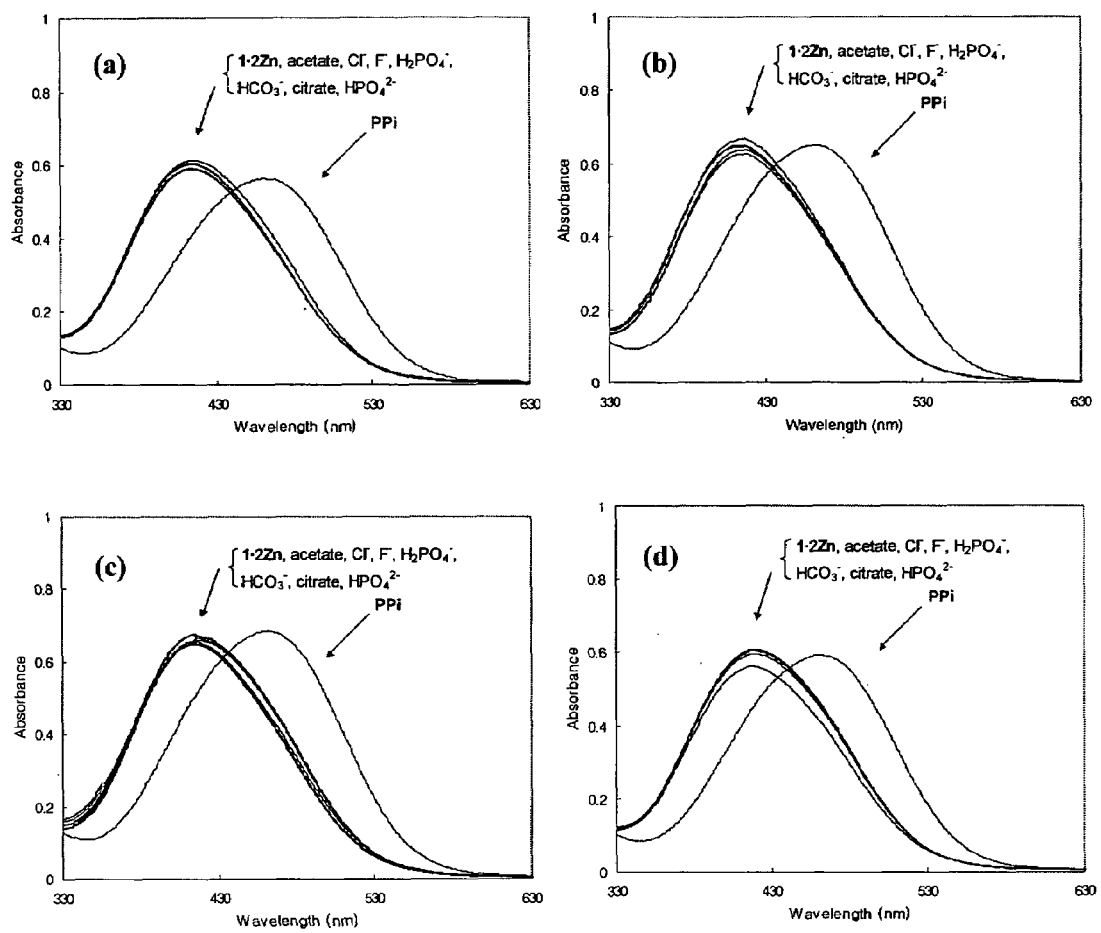
FIG. 4 is UV-vis spectra showing absorbance change of sensor 1•2Zn (30 μM) in pure aqueous buffered solvent at 25° C. in the presence of various anions (60 μM): (a) pH 6.5 (MES 10 mM); (b) pH 7.0 (HEPES 10 mM); (c) pH 7.4 (HEPES 10 mM); and (d) pH 8.3 (Tris-HCl 10 mM).

PH dependence of the sensor 1•2Zn in PPi sensing was tested and the results thereof were shown in FIG. 4. UV-vis absorption changes shown in FIG. 2(b) occurred in a wide pH range of 6.5-8.3 with a similar tendency. This result shows that even if the external pH is disturbed, sensor 1•2Zn can still detect PPi.

Figure 5:
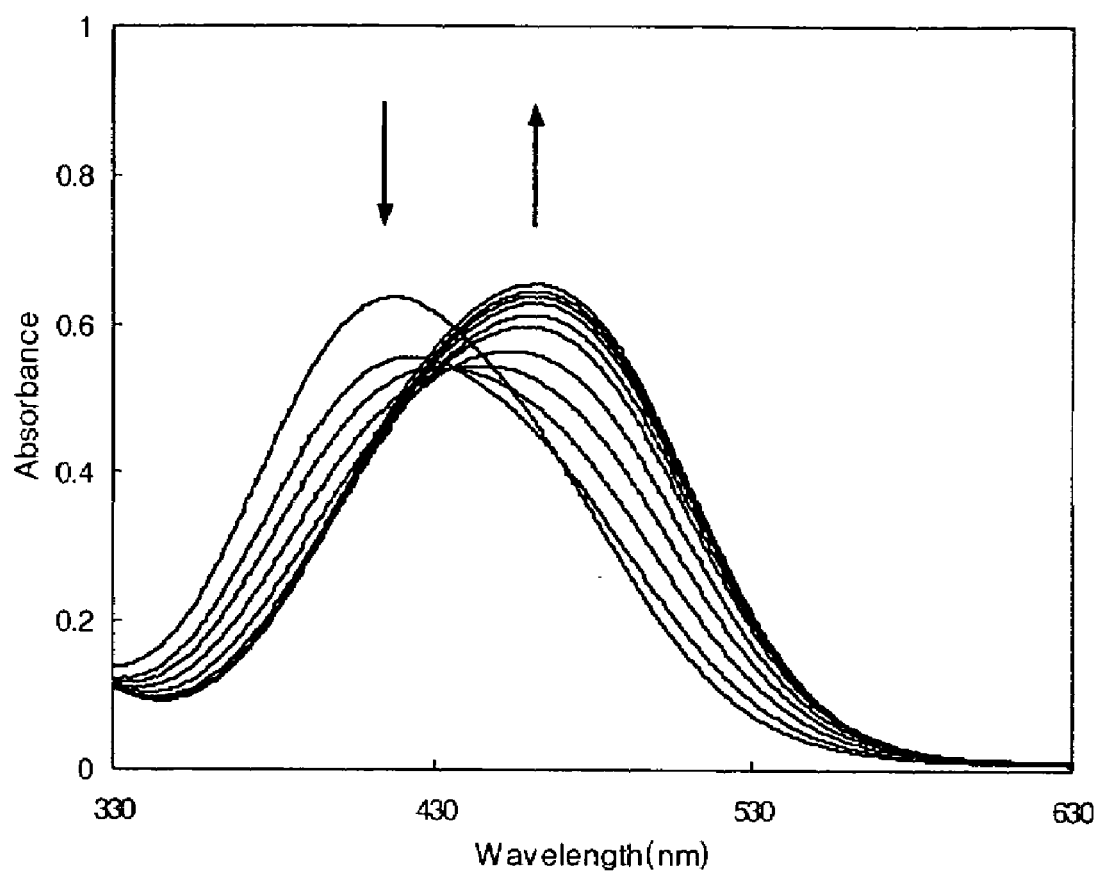
FIG. 5 is UV-vis spectra showing absorbance change of sensor 1•2Zn (30 μM) in the presence of $HPO_4^{2-}$ (300 μM) upon addition of PPi (Sodium salt): [PPi]=0, 4, 8, 12, 16, 20, 23, 28, 32, 40, 65 μM. The spectra were measured in pure aqueous solution of 10 mM HEPES buffer (pH 7.4) at 25° C.

FIG. 5 is UV-vis spectrum showing absorption change of sensor 1•2Zn in a presence of excess $HPO_4^{2-}$ upon addition of PPi(sodium salt), which also gave similar results with that of FIG. 2. This result implies that the sensor 1•2Zn is capable of PPi sensing even in the presence of excess $HPO_4^{2-}$.

E. Crystal Structure of the Complex Between Sensor 1•2Zn and PPi by X-Ray Diffraction and its Interpretation E-1) Crystal Growth and Identification of Crystal Structure Crystals suitable for X-ray diffraction study were grown by slow diffusion of the diethylether to aqueous methanol solution of sensor 1•2Zn complex with PPi (Potassium salt) at room temperature. X-ray data for single crystals were collected on an Enraf-Nonius Kappa CCD single crystal X-ray diffractometer at room temperature using graphite-monochromated Moka radiation ($\lambda$=0.71073 Å). Details of crystal data, data collection and structure refinement are listed in Table 1. The structures were solved by direct methods (SHELXS-97), and refined against all $F^2$ data (SHELXS-97).

TABLE 1

| | |
|---|---|
| Empirical formula | C38 H32 K N9 O16 P2 Zn2 |
| Formula weight | 1102.51 |
| Temperature | 293(2) K |
| Wavelength | 0.71073 Å |
| Crystal system | Triclinic |
| Space group | P$\bar{1}$ |
| Unit cell dimensions | a = 9.0250(10) Å, $\alpha$ = 102.370(2)°. |
| | b = 21.3150(10) Å, $\beta$ = 90.806(2)°. |
| | c = 27.4490(20) Å, $\gamma$ = 89.802(3)°. |
| Volume | 5157.2(7) Å$^3$ |
| Z | 4 |
| Density(calculated) | 1.420 Mg/m$^3$ |
| Absorption coefficient | 1.144 mm$^{-1}$ |
| F(000) | 2240 |
| Theta range for data collection | 1.62 to 27.04° |
| Limiting indices | $-10 \leq h \leq 10, -26 \leq k \leq 26,$ |
| | $-33 \leq l \leq 34$ |
| Reflections collected/unique | 21936/14251 [R(int) = 0.0983] |
| Completeness to theta = 27.04 | 62.9% |
| Refinement method | Full-matrix least-squares on F$^2$ |
| Data/restraints/parameters | 14251/2/955 |
| Goodness-of-fit on F$^2$ | 1.102 |
| Final R indices[I > 2$\sigma$(I)] | R1 = 0.1428, wR2 = 0.3956 |
| R indices (all data) | R1 = 0.3017, wR2 = 0.4369 |
| Largest diff. Peak and hole | 1.325 and $-0.901$ e.Å$^{-3}$ |

E-2) Interpretation of Crystal Structure

Figure 6:
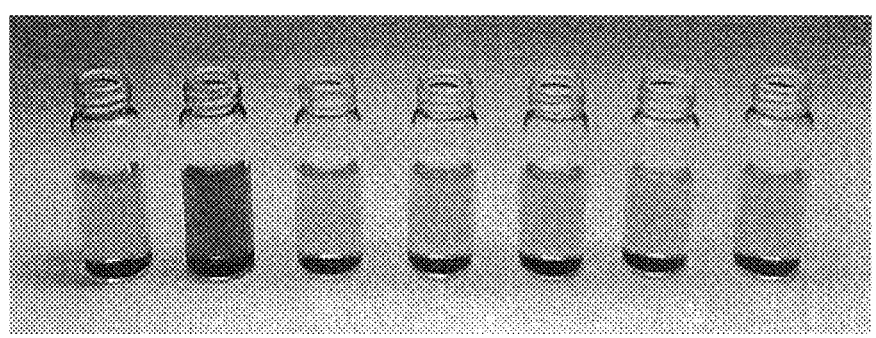
FIG. 6 is a photograph showing color changes of sensor 1•2Zn in 10 mM aqueous HEPES buffer solution (pH 7.4), [1•2Zn]=60 μM, [anion]=60 μM; from left to right; no anion, citrate, $HPO_4^{2-}$, $H_2PO_4^-$, acetate and $F^-$.

Crystal structure and novel binding mode of the complex between 1•2Zn and PPi, which was unambiguously elucidated by X-ray analysis, were shown in FIG. 8(a) and 8(b), respectively. The X-ray structure of the complex shown in FIG. 8(a) reveals that the two sets of oxygen anions on each P of PPi bind to the dinuclear zinc complex by bridging the two metal ions to give rise to the two hexa-coordinated $Zn^{2+}$ ions in 1•2Zn. The binding mode for $HPO_4^{2-}$-1•2Zn should be the same as that of $HPO_4^{2-}$—H-bpp. Despite this, $HPO_4^{2-}$ does not make a large UV-vis absorption change upon complexation with 1•2Zn. Instead, only PPi induces selective red-shift of $\lambda_{max}$ of 1•2Zn because weakening the bond between p-nitrophenylazo phenolate oxygen and $Zn^{2+}$ induces more negative charge character on the phenolate oxygen and thus the bathochromic shift of $\lambda_{max}$ of 1•2Zn occurs. As revealed by previous works, $HPO_4^{2-}$ does not coordinate in tetradentate fashion like PPi. This explains why $HPO_4^{2-}$ does not alter $\lambda_{max}$ of 1•2Zn. Stronger coordination of PPi to dinuclear zinc complex enables sensor 1•2Zn to show color changes and higher selectivity over $HPO_4^{2-}$ (FIG. 6). Hexacoordination of $Zn^{2+}$ ions is clearly reflected in extremely high $K_a$ of PPi-1•2Zn in water ($K^a$=6.6×10$^8$ M$^{-1}$). It is worthwhile noting that PPi binds 1•2Zn over 10$^3$-fold more tightly than $HPO_4^{2-}$ does.

Figure 7:
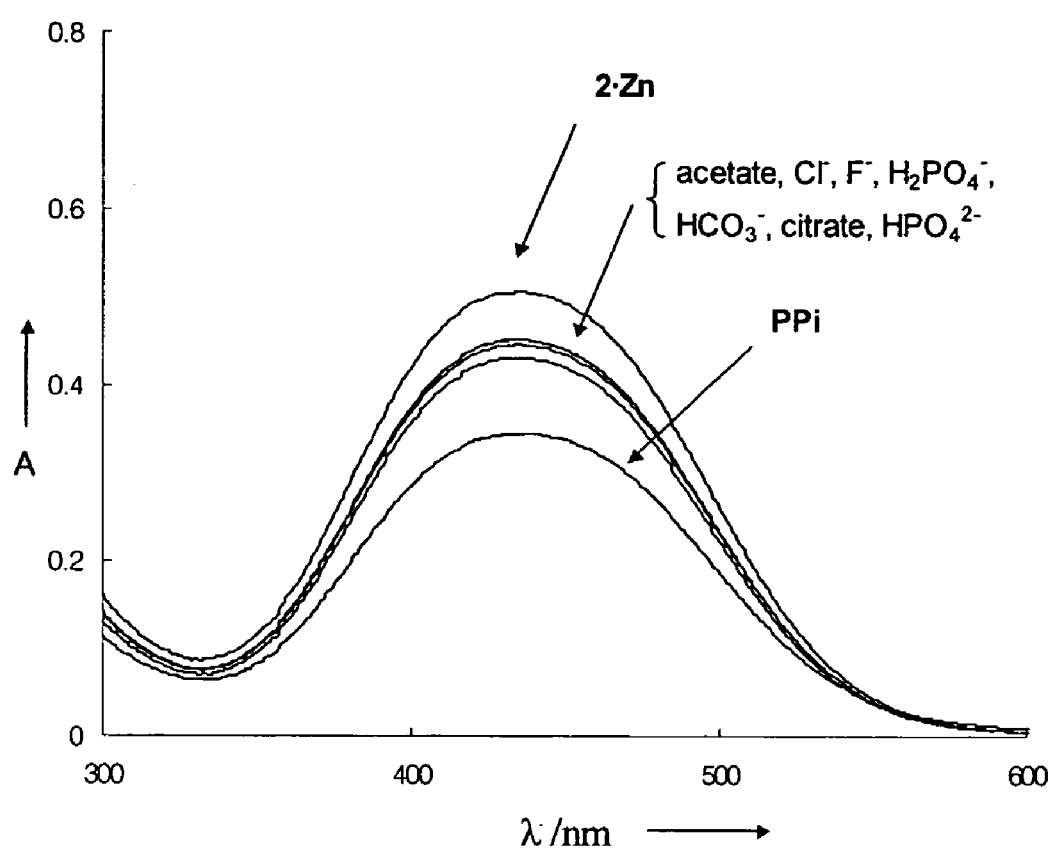
FIG. 7 is UV-vis spectra showing absorbance change of sensor 2•Zn (30 μM) in pure aqueous solution of 10 mM HEPES buffer (pH 7.4) at 25° C. in the presence of various anions (900 μM).

A control sensor, mononuclear 2•Zn does not show $\lambda_{max}$ and color changes upon the addition of PPi (FIG. 7). This result means that the cooperative action of two $Zn^{2+}$-Dpa (Dpa=bis(2-pyridylmethyl)amine) is needed for the selective sensing of PPi.

F. Fluorescence Test

Figure 9:
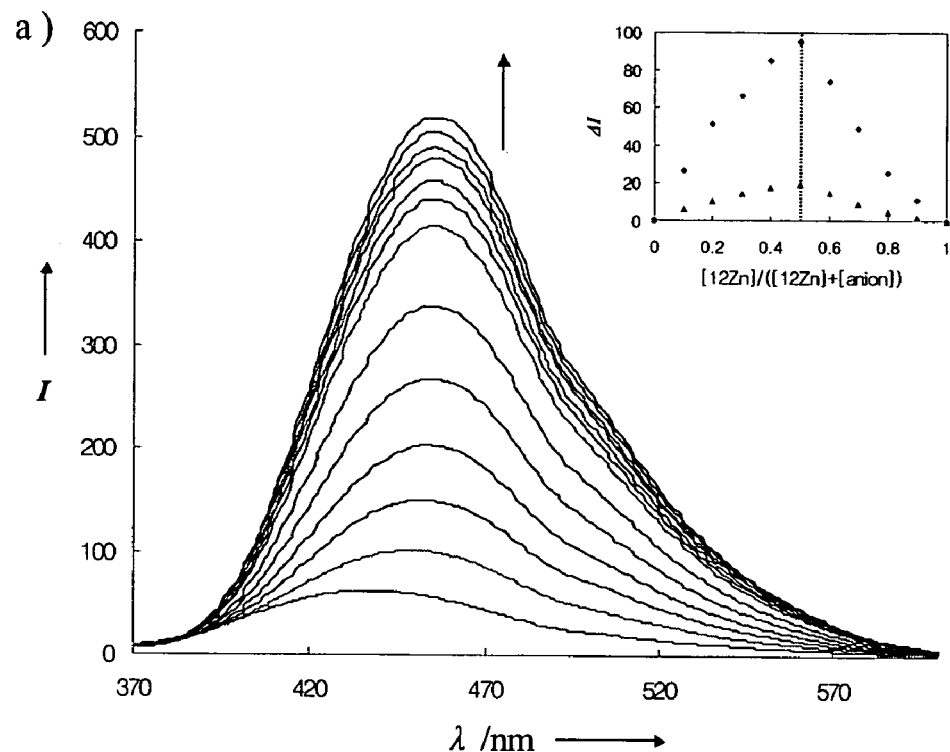
FIG. 9 is fluorescence spectra showing fluorescence intensity change of: (a) sensor 7•2Zn (6 μM) upon addition of PPi (Sodium salt): [PPi]=0, 0.6, 1.2, 1.8, 2.4, 3.0, 3.6, 4.2, 4.8, 5.4, 6.0, 6.6, 7.2, 7.8 μM. The spectra were measured in an aqueous solvent of 10 mM HEPES buffer (pH 7.4) at 25° C. (Inset) The Job's plot between 7•2Zn and anions: (□) PPi, (▲) ATP; and (b) sensor 7•2Zn (6 μM) in 10 mM HEPES buffer (pH 7.4) at 25° C. in the presence of various anions (8 μM)
Figure 9:
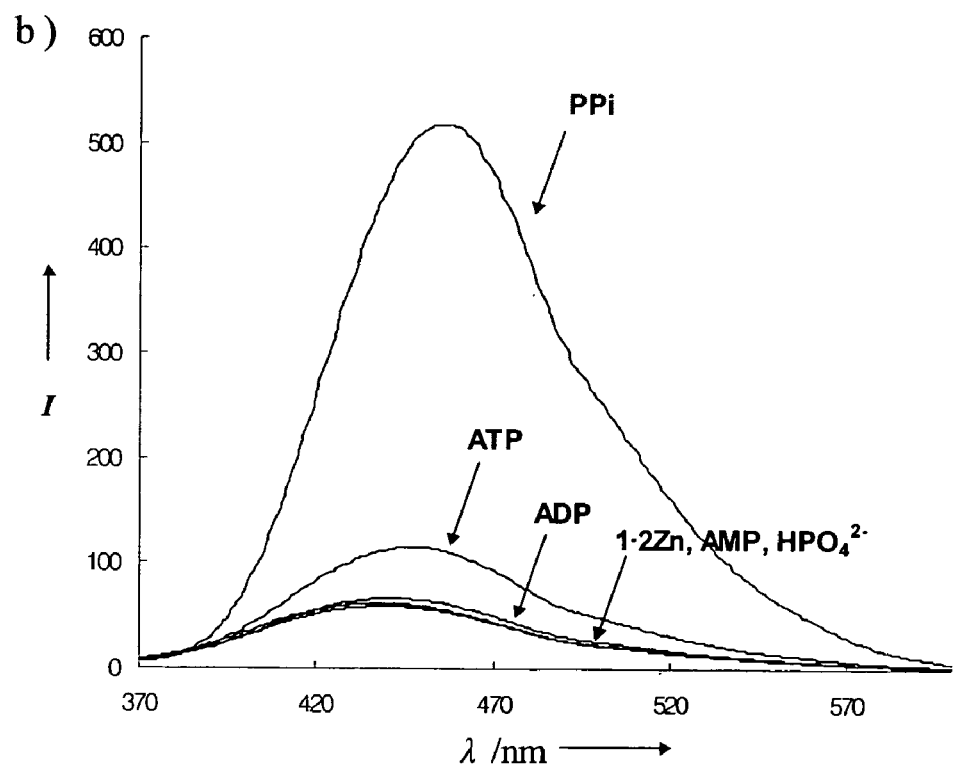

First, effect of anions (sodium salts) on a fluorescence spectrum of fluorescent sensor 7•2Zn was examined in an aqueous solution of 10 mM HEPES buffer (pH 7.4) at 25° C., and the results thereof were shown in FIG. 9. The concentration of the fluorescent sensor was adjusted to 6 $\mu$M. In the absence of an anion guest, the fluorescence spectrum of the sensor 7•2Zn was characterized by an intense band at 436 nm.

The fluorescent sensor 7•2Zn did not exhibit any obvious spectral change upon addition of AMP, $HPO_4^{2-}$ and even up to an excess of 100 equiv of other monovalent anions such as $CH_3CO_2^-$, $F^-$, $HCO_3^-$ and $Cl^-$. When PPi was added to an aqueous solution of 7•2Zn, the fluorescent emission spectrum shifted in a dose-dependent manner toward longer wavelengths. As shown in FIG. 9, the $\lambda_{max}$ shifted from 436 nm to 456 nm. Increasing the PPi concentration up to 1 equiv resulted in a 9.5-fold fluorescence enhancement. However, the addition of over 4 equiv of ATP showed only 2-fold enhancement accompanied by a 12 nm red shift. In the case of ADP, sensor 7•2Zn showed only a subtle emission change (1.5 fold increase) upon addition of a 50-fold excess ADP. The addition of AMP and $HPO_4^{2-}$ did not lead to an emission enhancement even after addition of 100 equiv of each anion.

The Job's plot for the binding between 7•2Zn and anions (PPi and ATP) showed a 1:1 stoichiometry (inset of FIG. 9(a)). The apparent association constant ($K_a$) was determined to be (2.9±0.7)×10$^8$ M$^{-1}$ for PPi-7•2Zn by a standard algorithm for competitive binding in the presence of excess $HPO_4^{2-}$ in an aqueous solvent of 10 mM HEPES buffer (pH 7.4) at 25° C. By the same method, $K_a$ for ATP-7•2Zn was found to be (7.2±1.0)×10$^6$ M$^{-1}$, which is 40-fold lower than PPi-7•2Zn. This means that 7•2Zn can even detect PPi at nanomolar concentrations in water.

Figure 10:
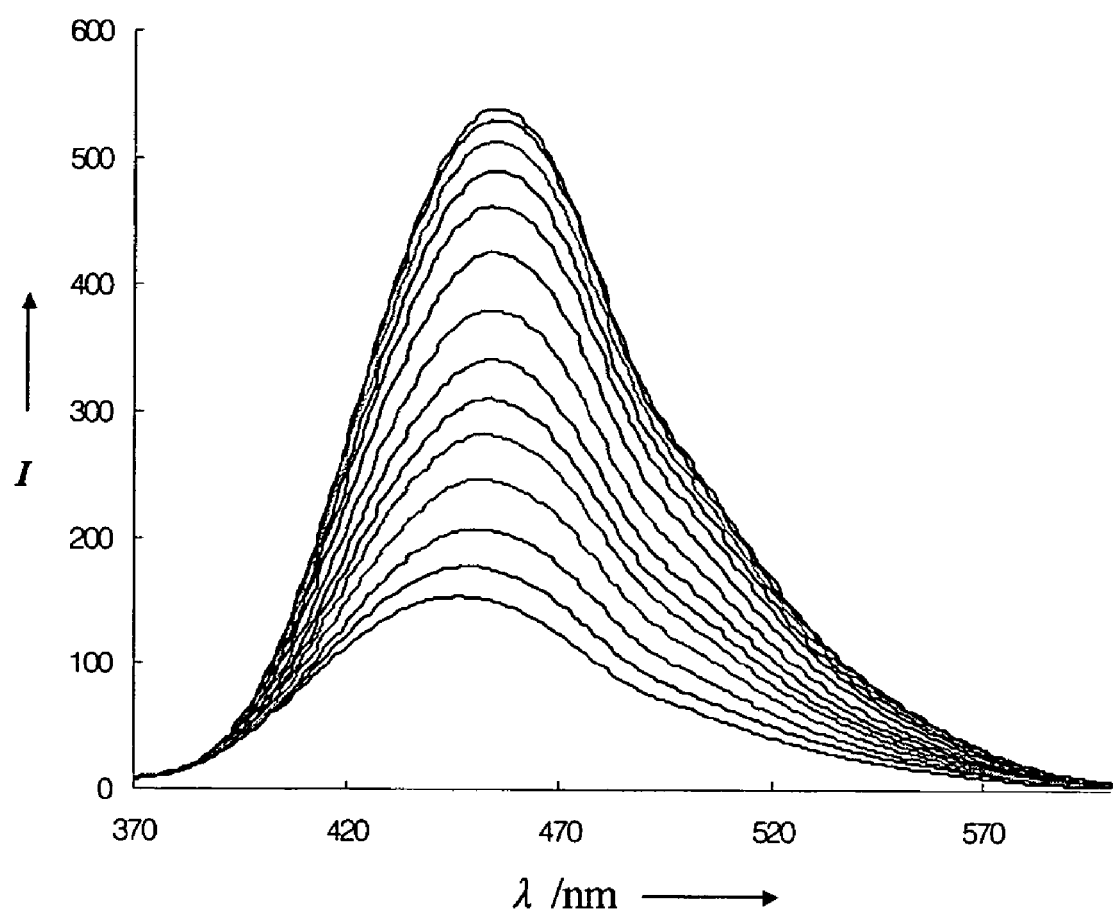
FIG. 10 is fluorescence spectra showing fluorescence intensity change of sensor 7•2Zn (6 μM) in the presence of ATP (300 μM) upon addition of PPi (Sodium salt): [PPi]=0, 1.2, 2.4, 3.6, 4.8, 6.0, 8.0, 11, 17, 24, 34, 45, 65, 85 μM. The spectra were measured in a pure aqueous solution of 10 mM HEPES buffer (pH 7.4) at 25° C.

FIG. 10 shows that 7•2Zn can detect less than 1 equiv of PPi even in the presence of a 50- to 250-fold excess of ATP (based on the amount of PPi detected). In other words, 7•2Zn can selectively detect PPi in an aqueous solution with remarkable selectivity over ATP with a detection limit at micromolar concentrations. There are many biochemical reactions which release PPi in the presence of ATP. Therefore, in order to develop PPi sensors for bioanalytical applications, we need to develop a sensor that can detect a small amount of PPi in the presence of a large excess of ATP. This result implies that our sensor can be used in bioanalytical applications.

The binding mode for PPi-7•2Zn is believed to be almost identical with that of PPi-1•2Zn. The complex would show that the two sets of oxygen anions on each P of PPi bind to the dinuclear zinc complex by bridging the two metal ions to give rise to two hexa-coordinated $Zn^{2+}$ ions in 7•2Zn. PPi induces a pronounced red shift of $\lambda_{max}$ of 7•2Zn because the weakening of the bond between the phenolate oxygen and $Zn^{2+}$ induces a more negative charge characteristic on the phenolate oxygen. Simultaneously, an increased charge characteristic on the phenolate oxygen is transferred through the benzene ring to the naphtyl group, and induces a fluorescent enhancement of the naphtyl group.

The selectivity for PPi over ATP can be understood on the basis of the structure of the guest. In the case of ATP, one neutral oxygen among O—P bonds has to participate in binding with 7•2Zn. Therefore, the binding affinity of ATP is drastically reduced and the degree of fluorescence change becomes smaller relative to PPi binding.

A control sensor, mononuclear 7•Zn does not show emission $\lambda_{max}$ shift and fluorescent enhancement upon addition of PPi. This result means that the cooperative action of two $Zn^{2+}$-Dpa is needed for the selective sensing of PPi.

Figure 11:
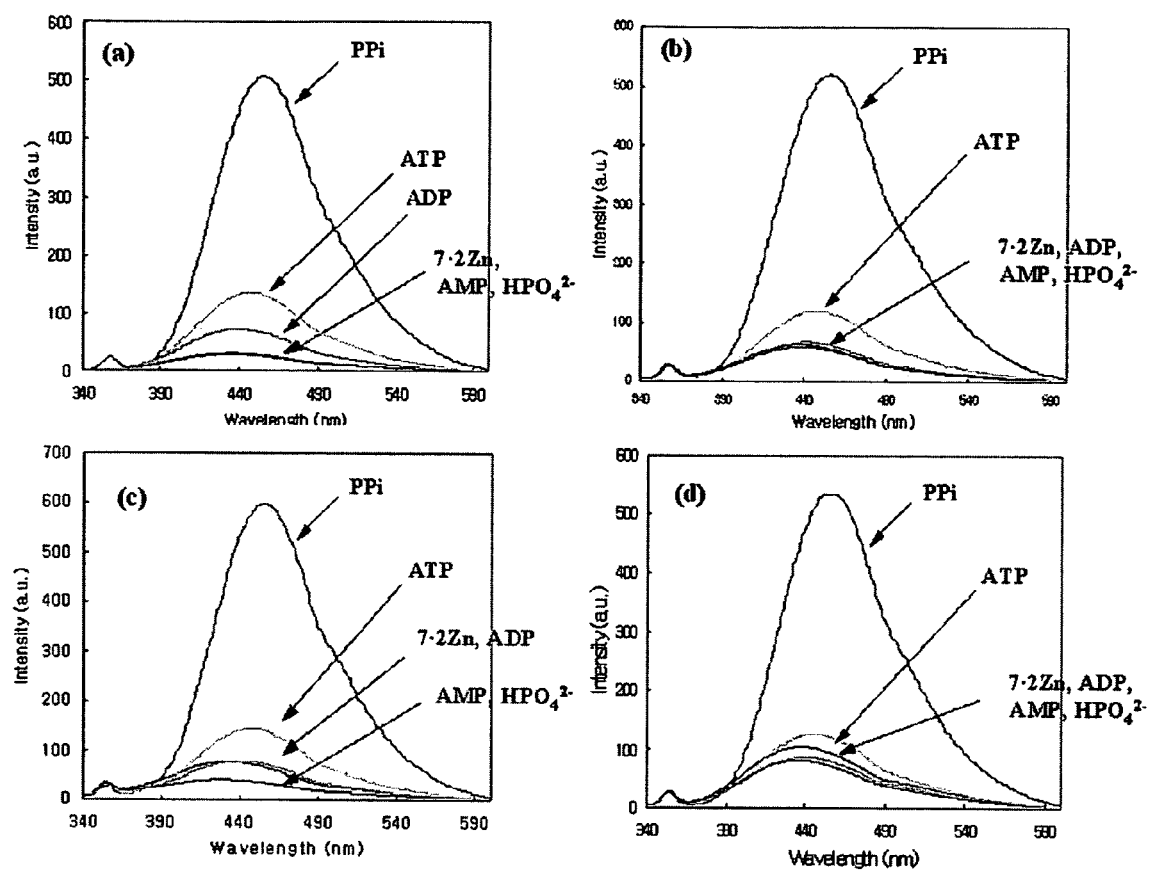
FIG. 11 is fluorescence spectra showing fluorescence intensity change of sensor 7•2Zn (6 μM) in pure aqueous buffered solvent at 25° C. in the presence of various anions (12 μM): (a) pH 6.5 (MES 10 mM); (b) pH 7.4 (HEPES 10 mM); (c) pH 8.3 (Tris-HCl 10 mM); and (d) pH 10.1 (CHES 10 mM).

PH dependence of sensor 7•2Zn in PPi sensing was tested. Fluorescence intensity changes shown in FIG. 9 occurred in a wide pH range of 6.5-10.1 with a similar tendency. This result shows that even if the external pH is disturbed, sensor 7•2Zn can still detect PPi (FIG. 11).

G. Cyclic Voltammetry Test

Figure 12:
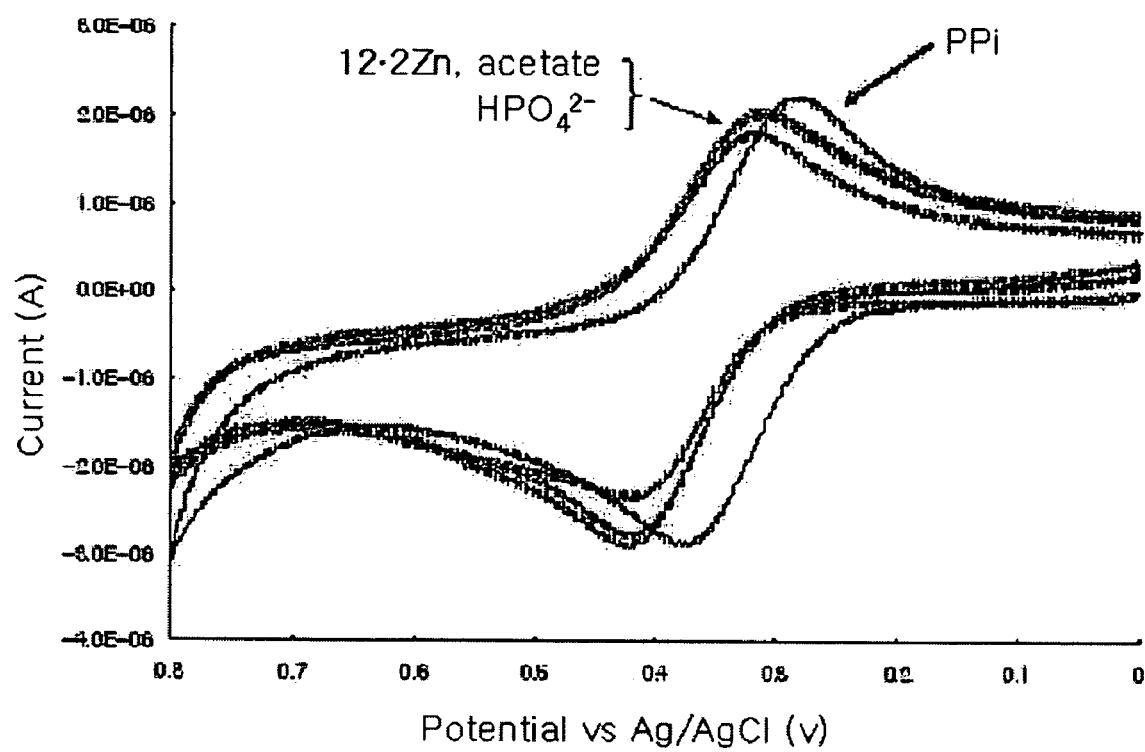
FIG. 12 is cyclic voltammogram of sensor 12•2Zn in the presence of various anions.

Effect of anions (sodium salts) on electrochemical properties of electrochemical sensor 12•2Zn was examined with cyclic voltammetry in an aqueous system of 10 mM HEPES buffer (pH 7.4) at 25° C. 3-electrode system (working electrode: glassy carbon working electrode, reference electrode: Ag/Ag$^+$, counter electrode: Pt wire) was used. Potential was increased at a rate of 50 mV/s in a range of 0-0.8V. The concentration of the fluorescent sensor was adjusted to 0.3 mM. The result was shown in FIG. 12. As shown in FIG. 12, cyclic voltammogram of the electrochemical sensor 12•2Zn exhibited reversible redox couples of ferrocene/ferricinium.

Figure 8:
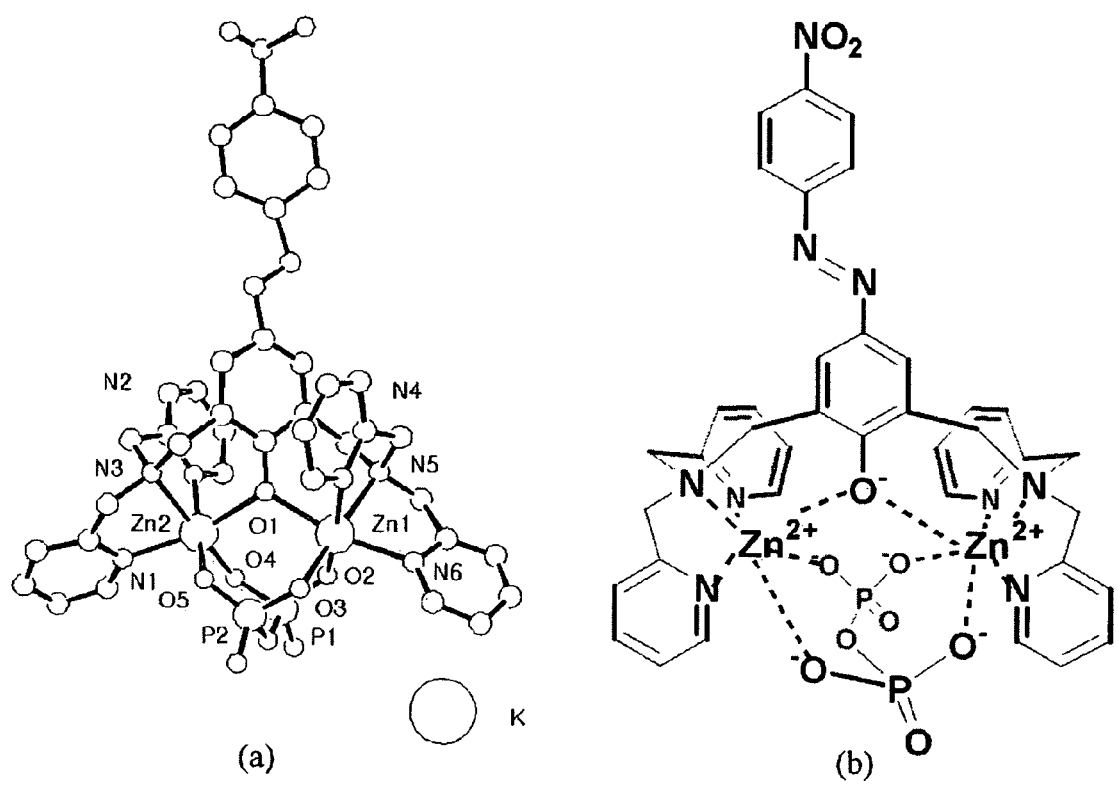
FIGS. 8(a) and 8(b) are X-ray crystallography showing the crystal structure and the binding mode of the complex between the dinuclear zinc complex of the compound 1 and PPi. Hydrogen atoms have been omitted for clarity.

The electrochemical sensor 12•2Zn did not exhibit any obvious change in cyclic voltammogram upon addition of monovalent anions such as $H_2PO_4^-$ and $CH_3CO_2^-$. Moreover, no detectable change was observed upon addition of dibasic anion $HPO_4^{2-}$. When PPi was added to an aqueous solution of 12•2Zn, however, the oxidation and reduction wave was observed at a lower potential. It was remarkable that the cyclic voltammogram was no longer affected by the addition of more than 1.2 equiv. of PPi. Since the sensors 1•2Zn, 7•2Zn, 12•2Zn have common anion-binding sites, crystal structure and stoichiometry, association constant ($K_a$) of 12•2Zn are believed to be the actually identical with that of the sensor 1•2Zn or 7•2Zn. The sensor 12•2Zn would bind to PPi in a 1:1 stoichiometry and have a similar binding mode as shown in FIG. 8. Even not calculated in the cyclic voltammetry due to its very high value, the association constant ($K_a$) of PPi-12•2Zn is expected to have about $1.0×10^8$ M$^{-1}$. These results imply that the sensor 12•2Zn can selectively detect PPi with remarkable selectivity over other anions, and that the sensor 12•2Zn is an electrochemical one which produces an electrochemical signal in response to the presence of the PPi.

In summary, we have developed a new dinuclear metal complex which is useful for pyrophosphate assay, wherein as the complex binds to the anion, the coordination of the electron donating group with the metal is weakened, and reinforced electron donation by the electron donating group is transferred through the conjugation ring system to the indicating group to generate a detectable indicating signal concomitant with the change of its electronic density. The dinuclear metal complex shows high sensitivity and high selectivity for pyrophosphate over other anions in an aqueous solvent over a wide pH range. This system shows good selectivity for PPi even in the presence of a strong competitor such as $HPO_4^{2-}$ or ATP. Therefore, it can be used as a pyrophosphate sensor in bioenergetic and metabolic processes. Specifically, it can be applicable to an enzyme assay with the con-comitant release of PPi, for example, in the conversion of ATP to AMP, a DNA sequencing with the con-comitant release of PPi in pyrosequencing process, PCR (polymerase chain reaction) monitoring with the con-comitant release of PPi in the PCR process. For example, prenyltransferase which produces pyrophosphate from its derivatives can be assayed. In addition, it can be used for the development of biochips therefor.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

REFERENCES (1) (a) Brzzka, Z. In *Comprehensive Supramolecular Chemistry* Atwood, J. L., Davies, J. E. D., MacNicol, D. D., Vgtle, F., Suslick, K, S., Eds.; Pergamon: Oxford, 1996; pp 187-212 (b) *Chemosensors of Ion and Molecular recognition* Desvergne, J.-P., Czarnik, A. W., Eds.; Kluwer: Dordrecht, 1997, Vol 492. (c) Schmidtchen, F. P.; Berger, M. *Chem. Rev.* 1997, 97, 1609-1646. (d) Beer, P. D. *Acc. Chem. Res.* 1998, 31, 71-80. (e) *Supramolecular chemistry for anions* Binachi, K., Bowman-James, K., Garcia-Espana, E., Eds.; New York, 1997. (f) Lehn, J.-M. *Supramolecular chemistry, Concepts and Perspectives;* VCH: Weinheim, 1995.

(2) Limpcombe, W. N. Strter, N. *Chem. Rev.* 1996, 96, 2375-2434.

(3) (a) McCarty, D. J. *Arthritis. Rheum.* 1976, 19, 275-285 (b) Caswell, A.; Guilland-Cumming, D. F.; Heam, P. R.; McGuire, M. K.; Russell, R. G. *Ann. Rheum. Dis.* 1983, 42 (suppl 1), 27-37. (c) Doherty, M. *Ann. Rheum. Dis.* 1983, 42(suppl 1), 38-44.

(4) (a) Kubo, Y.; Maeda, S.; Tokita, S.; Kubo, M. *Nature.* 1996, 382, 522-523. (b) Niikura, K.; Metzger, A.; Anslyn, E. V. *J. Am. Chem. Soc.* 1998, 120, 8533-8534. (c) Lavigene, J. J.; Anslyn, E. V. *Angew. Chem. Int. Ed. Engl.* 1999, 38, 3666-3669. (d) Fabbrizzi, L.; Licchelli, M.; Rabioli, G.; Taglietti, A. *Coord. Chem. Rev.* 2000, 205, 85-108. (e) Zhong, Z.; Anslyn, E. V. *J. Am. Chem. Soc.* 2002, 124, 9014-9015.

(5) PPi sensors in aqueuous solution: (a) Vance, D. H.; Czarnik, A. W. *J. Am. Chem. Soc.* 1994, 116, 9397-9398. (b) Czarnik, A. W. *Acc. Chem. Res.* 1994, 27, 302-308. (c) Mizukami, S.; Nagano, T.; Urano, Y.; Odani, A.; Kikuchi, K. *J. Am. Chem. Soc.* 2002, 124, 3920-3925. (d) Fabbrizzi, L.; Marcotte, N.; Stomeo, F.; Taglietti, A. *Angew. Chem. Int. Ed. Engl.* 2002, 41, 3811-3814.

(6) PPi sensors in MeOH and aqueous $CH_3CN$: (a) Nishizawa, S.; Kato, Y. Teramae, N. *J. Am. Chem. Soc.* 1999, 121, 9463-9464. (b) Anzenbacher, P. Jr.; Jurskov, K. Sessler, J. L. *J. Am. Chem. Soc.* 2000, 121, 9350-9351.

The invention claimed is:

1. A dinuclear metal complex of a compound, wherein the compound comprises a conjugation ring system substituted with:
  a) an electron donating group selected from —OH, —SH and —NH$_2$;
  b) an indicating group selected from a chromogenic group, a fluorescent group and an electrochemical group; and
  c) two binding auxiliary groups, in combination with the electron donating group each of which being coordinated with the metal to provide an anion bonding site, wherein as the complex binds to a anion, the coordination of the electron donating group with the metal is weakened and electron donation of the electron donating group to the conjugation ring system is reinforced such that the reinforced electron donation by the electron donating group is transferred through the conjugation ring system to the indicating group to produce an indicating signal concomitant with the change of its electronic density.

2. The complex of claim 1, wherein the compound has formula I:

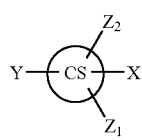

wherein, X is an electron donating group selected from —OH, —SH and —NH$_2$; Y is an indicating group selected from a chromogenic group, a fluorescent group and an electrochemical group; $Z_1$ and $Z_2$ are binding auxiliary groups, both of which are each independently hydrocarbons containing at least one atom selected from the group consisting of N, O, S and P; and

is a conjugation ring system.

3. The complex of claim 1, wherein the conjugation ring system is an aromatic ring system.

4. The complex of claim 1, wherein the conjugation ring system is a benzene ring system in which each of the two binding auxiliary groups is substituted at an ortho position and the indicating group is at a para position relative to the electron donating group.

5. The complex of claim 1, wherein the compound has formula II:

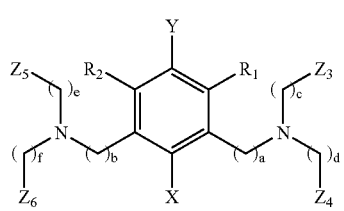

wherein, X is an electron donating group selected from —OH, —SH and —NH$_2$; Y is an indicating group selected from a chromogenic group, a fluorescent group and an electrochemical group; $Z_3$, $Z_4$, $Z_5$ and $Z_6$ are each independently hydrocarbons containing at least one atom selected from the group consisting of N, O, S and P; $R_1$ and $R_2$ are each independently selected from the group consisting of hydrogen, halogen, hydroxyl, amino, alkyl, alkoxy, thioalkyl, alkylamino, imine, amide, phosphate, phosphine, carbonyl, carboxyl, silyl, ether, thioether, sulfonyl, selenoether and ketone; and a, b, c, d, e and f are each independently integers of 1 to 3.

6. The complex of claim 5, wherein $Z_3$, $Z_4$, $Z_5$ and $Z_6$ are each independently selected from the group consisting of —NR$_3$R$_4$, —OR$_5$, —SR$_6$, —PR$_7$R$_8$, a hetero aliphatic cycle and a heteroaromatic ring, in which R$_3$, R$_4$, R$_5$, R$_6$, R$_7$ and R$_8$ are each independently an alkyl or a substituted alkyl.

7. The complex of claim 5, wherein $Z_3$, $Z_4$, $Z_5$ and $Z_6$ are each independently heteroaromatic ring having a formula:

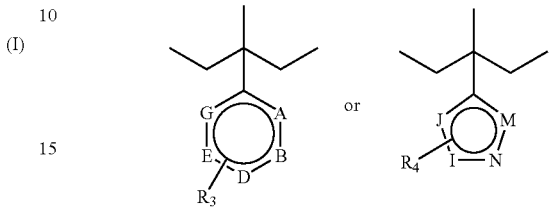

wherein, at least one of A, B, D, E and G is nitrogen, and the others are oxygen or carbon, and at least one of I, J, M and N is oxygen and the others are nitrogen or carbon; and R$_3$ and R$_4$ are each independently selected from the group consisting of a hydrogen, a halogen, a hydroxyl, an amino, an alkyl, an alkoxy, a thioalkyl, an alkylamino, an imine, an amide, a phosphate, a phosphine, a carbonyl, a carboxyl, a silyl, an ether, a thioether, a sulfonyl, a selenoether and a ketone.

8. The complex of claim 1, wherein the anion is pyrophosphate.

9. The complex of claim 1, wherein the metal is selected from the group consisting of Zn, Fe, Mn, Cu, Co, Hg, Pb, Ce, Cd and Mg.

10. The complex of claim 1, wherein the metal is selected from the group consisting of Zn, Co, Fe, Cd and Cu.

11. The complex of claim 1, wherein the metal is Zn.

12. The complex of claim 1, wherein the metal is hexa-coordinated when the complex binds to the anion.

13. The complex of claim 1, wherein the electron donating group is —OH.

14. A method for assaying pyrophosphate anion comprising:
   a) adding a pyrophosphate sensor to a sample to be tested to generate an detectable indicating signal; and
   b) detecting the indicating signal to quantify the pyrophosphate anion;
   wherein the pyrophosphate sensor is the dinuclear metal complex of claim 1.

15. The method of claim 14, wherein the pyrophosphate sensor is the dinuclear metal complex of claim 2.

16. The method of claim 14, wherein the pyrophosphate sensor is the dinuclear metal complex of claim 3.

17. The method of claim 14, wherein the assay is carried our in an aqueous system.

18. The method of claim 14, wherein the assay is used in bioanalytical applications involving release of the pyrophosphate.

19. The method of claim 18, wherein the bioanalytical applications include an enzyme assay, a DNA sequencing, or monitoring of polymerase chain reaction.

20. The method of claim 14, wherein the pyrophosphate sensor is used in a form of a biochip to which the pyrophosphate sensor is attached.

* * * * *